(12) United States Patent
Mitra

(10) Patent No.: US 7,825,086 B2
(45) Date of Patent: *Nov. 2, 2010

(54) ACYCLOVIR-PEPTIDE ANALOGS

(75) Inventor: Ashim K. Mitra, Overland Park, KS (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/194,248

(22) Filed: Aug. 19, 2008

(65) Prior Publication Data

US 2009/0082566 A1    Mar. 26, 2009

Related U.S. Application Data

(60) Division of application No. 10/854,533, filed on May 26, 2004, now Pat. No. 7,553,812, which is a continuation of application No. PCT/US02/38846, filed on Dec. 4, 2002.

(60) Provisional application No. 60/336,666, filed on Dec. 4, 2001.

(51) Int. Cl.
| | |
|---|---|
| A61K 38/16 | (2006.01) |
| A61K 38/00 | (2006.01) |
| A61K 51/00 | (2006.01) |

(52) U.S. Cl. .............................. 514/8; 424/1.69; 514/2
(58) Field of Classification Search .................. None
See application file for complete search history.

(56) References Cited

U.S. PATENT DOCUMENTS 7,553,812 B2 *  6/2009  Mitra ........................... 514/8
2009/0149482 A1 *  6/2009  Mitra et al. ............ 514/263.37

* cited by examiner

*Primary Examiner*—Maury Audet
(74) *Attorney, Agent, or Firm*—Stinson Morrison Hecker LLP

(57) ABSTRACT

Dipeptide and tripeptide ester derivatives of acyclovir and its analogs are disclosed which are useful to treat herpes virus infections. Also disclosed is a method for preparing a therapeutic agent for targeted delivery to ocular tissue comprising linking the therapeutic agent to one or more groups of the formula —X—Y-$Z_{(n)}$-R; wherein each X, Y and Z is independently Met, Val, Thr, Tyr, Trp, Ser, Ala or Gly; each R is independently H or an amino-protecting group; and each n is independently 0 or 1.

27 Claims, 18 Drawing Sheets

ACYCLOVIR-PEPTIDE ANALOGS

PRIORITY OF INVENTION

This application is a division of U.S. application Ser. No. 10/854,533, filed on May 26, 2004 now U.S. Pat. No. 7,553,812, which is a continuation under 35 U.S.C. 111(a) of International Application No. PCT/US02/38846 filed Dec. 4, 2002 and published in English as WO 03/048190 A2 on Jun. 12, 2003, which claims priority to U.S. Provisional Application Ser. No. 60/336,666, filed Dec. 4, 2001, which applications and publication are incorporated herein by reference.

GOVERNMENT FUNDING

This invention was made with the assistance of the National Institutes of Health under grant nos. EY 09171 and EY 10659. The U.S. Government has certain rights in the invention.

BACKGROUND OF THE INVENTION

Infection with herpes simplex virus is the single most frequent cause of corneal opacities in developed countries (D. L. Easty, *Clinical Aspects of Ocular Herpes Simplex Virus Infection*, Yearbook Medical Publ. (1985) at pages 135-178). Currently available therapy for HSV keratitis involves the use of a 1% trifluorothymidine (TFT) solution. However, one of the major problems associated with TFT therapy is its cytotoxicity, restricting its use in long-term treatment.

In superficial herpes keratitis, the efficacy of a 3% ophthalmic ointment of acyclovir (ACV) applied 5 times a day for up to 14 days has been reported (D. M. Richards et al., *Drugs*, 26, 378 (1983)). However due to the various problems associated with the use of ointments in the eye, ACV has not been approved for clinical use in HSV keratitis patients in the United States. In addition, ACV ointment is not effective against stromal keratitis or when the deeper ocular tissues are involved (J. J. Sanitato et al., *Am. J. Opthalmol.*, 98, 537 (1984)). This observation suggests that ACV has poor permeation characteristics across the corneal epithelium. The corneal epithelium is composed of 5 to 6 layers of columnar epithelium with tight junctions, and hence paracellular diffusion across this epithelium is minimal. Beneath the epithelial layer is the stroma, which contains more than 90% water, and hence presents a barrier to hydrophobic compounds.

In order to circumvent the problem of poor permeation of ACV, the use of highly lipophilic ACV acyl ester derivatives to increase the corneal permeation and regeneration of ACV has been evaluated. The lipophilic esters of ACV exhibit better corneal permeability than ACV alone and these monoacyl ester derivatives produce higher levels of ACV in the aqueous humor of rabbit eyes (P. M. Hughes et al., *J. Ocul. Pharmacol.*, 9, 299 (1993)). However, due to their enhanced lipophilicity, these compounds are poorly soluble in water. Therefore, their formulation into eye drops is difficult.

L. M. Beauchamp et al., *Antiviral Chem. and Chemother.*, 3, 157 (1992) and L. Colla et al., *J. Med. Chem.*, 26, 602 (1983) reported the preparation of 18 mono-amino acid esters of ACV as potential prodrugs for oral administration. The most promising of these, valacyclovir (Val-ACV), the valine ester of ACV, is a hydrophilic prodrug of ACV. However, its solution stability limits its use in HSV-keratitis.

In addition to ACV, ganciclovir (GCV) is another antiviral compound that is effective against the herpes viruses that cause ophthalmic disease. GCV is particularly effective against human cytomegalovirus (CMV). However, GCV is expected to have the same problems as ACV in reaching the ocular tissues with topical or systemic administration.

Membrane transporters and receptors have recently been reported in certain tissues. Solute transport via a transporter or a receptor is a mechanism of translocating hydrophilic compounds across lipid bilayers. However, little is known about the presence of various transporters and receptors on the corneal epithelium.

Drug delivery to the retina has received less attention than drug delivery to the cornea. Ocular drug therapy has so far involved primarily the anterior segment via local approaches. More than half of the existing ocular diseases occur within the back of the globe, yet a huge disparity exists between the number of drugs developed for the anterior segment versus those developed for the vitreo-retinal segment. Diseases affecting the retino-choroidal tissues include diabetic and proliferative vitreal retinopathies, CMV retinitis, and others.

Systemic delivery (e.g., intravenous or oral) is potentially an effective route of drug delivery to the eye. However, drugs administered by this route must cross the blood ocular barrier in order to reach the inner ocular tissues. The blood ocular barriers, like the blood brain barrier (BBB), restrict the movement of drug molecules into the eye from systemic circulation. The blood ocular barrier can be viewed as two barriers: the blood aqueous barrier (BAB) and the blood retinal barrier (BRB). The BAB consists of an epithelial barrier formed by the tight junctions of the non pigmented epithelial cells in the ciliary body and the posterior iridial epithelium and an endothelial barrier in the iridial vessels. The BRB consists of an outer retinal barrier formed by the retinal pigmented epithelium and an inner retinal barrier formed by the endothelial membrane of the retinal vessels. Though many drugs are delivered topically for anterior segment diseases, systemic delivery may be a more effective approach in treating patients with retinal and extra-ocular infections.

Therefore, in spite of the above reports, a need exists for antiviral compounds that are effective topically when applied to the eye, while exhibiting sufficient hydrophilicity to be formulated into solutions such as eye drops. A need also exists for antiviral compounds that reach both the anterior segment and the vitreo-retinal segment or the retina of the eye when administered systemically.

SUMMARY OF THE INVENTION

The present invention provides di- and tri-peptide mono- and di-esters of acyclovir and gancyclovir and their derivatives. These esters have sufficient hydrophilicity to be formulated into pharmacologically active compositions, such as aqueous solutions, e.g., eye drops. Compounds of the invention can be effectively transported into the ocular tissues. Specifically, such compounds effectively reach the anterior segment and/or the vitreo-retinal segment when administered either topically or systemically.

Accordingly, the present invention provides a compound of the invention, which is a compound of formula (I):

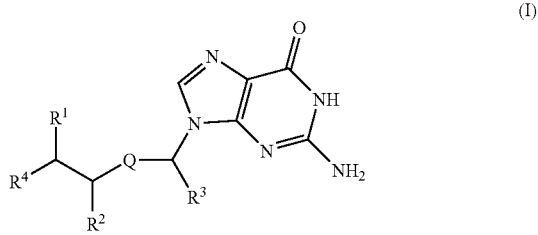

wherein $R^1$ is H, $(C_1-C_4)$alkyl, $(C_3-C_6)$cycloalkyl, hydroxy $(C_1-C_4)$alkyl, benzoyl$(C_1-C_4)$alkyl or phenyl; $R^2$ is H, OH, hydroxy($C_1$-$C_4$)alkyl, ($C_1$-$C_4$)alkyl or —$CH_2R^a$; $R^3$ is H, ($C_1$-$C_4$)alkyl or hydroxy($C_1$-$C_4$)alkyl; $R^4$ is OH or $R^a$; wherein each $R^a$ is independently -Q-X—Y-$Z_{(n)}$-R; each Q is independently S or O; each X, Y and Z is independently Met, Val, Thr, Tyr, Trp, Ser, Ala or Gly; each R is independently H or an amino-protecting group; and each n is independently 0 or 1; wherein at least one of $R^2$ and $R^4$ is $R^a$; or a pharmaceutically acceptable salt thereof.

The invention also provides a pharmaceutical composition comprising a compound of the invention and a pharmaceutically acceptable carrier. In particular embodiments, the carrier is a liquid or an ointment.

The present invention also provides the use of a compound of the invention in medical therapy.

The present invention also provides the use of a compound of the invention to prepare a medicament useful to treat a viral infection in a mammal.

The present invention also provides a method of treating a viral infection comprising administering to a mammal in need of such treatment an effective amount of a compound of the invention.

Some of the compounds of formula (I) are useful as intermediates for the preparation of other compounds of formula (I), as shown below. Novel methods and intermediates used to prepare a compound of the invention are also within the scope of the invention.

One embodiment of the present invention also provides a method for preparing a therapeutic agent for targeted delivery to ocular tissue comprising linking the therapeutic agent to one or more (e.g., 1, 2, 3, or 4) groups of the formula —X—Y-$Z_{(n)}$-R; wherein each X, Y and Z is independently Met, Val, Thr, Tyr, Trp, Ser, Ala or Gly; each R is independently H or an amino-protecting group; and each n is independently 0 or 1.

Another embodiment of the present invention provides a therapeutic agent linked to one or more (e.g., 1, 2, 3, or 4) groups of the formula —X—Y-$Z_{(n)}$-R; wherein each X, Y and Z is independently Met, Val, Thr, Tyr, Trp, Ser, Ala or Gly; each R is independently H or an amino-protecting group; and each n is independently 0 or 1.

In one embodiment, this invention provides novel dipeptide or tripeptide mono-ester derivatives of acyclovir (ACV), 2-amino-1,9-dihydro-9-[(2-hydroxyethoxy)methyl]-6H-purin-6-one (Zovirax®). The invention also provides novel dipeptide or tripeptide mono- or di-ester derivatives of ganciclovir (GCV), 2-amino-1,9-[[2-hydroxy-1-(hydroxymethyl)ethyl)ethoxy]methyl]-6H-purin-6-one, and other ACV analogs.

The compounds of the invention are effective against viral infections. The compounds of the invention are particularly effective against the herpes group of viruses, which includes, e.g., herpes simplex types 1 and 2, varicella zoster virus (VZV) and human cytomegalovirus (HCMV). The compounds of the invention are particularly effective against epithelial and stroma keratitis caused by HSV-1.

Without wishing to be bound by theory, it is believed that the peptide portions of compounds of the invention bind to receptors and thereby assist cellular internalization of the compounds of the invention. It is believed also that the compounds of the invention may function as prodrugs, being hydrolyzed intracellularly and releasing acyclovir or ganciclovir, which under this theory would be responsible for the biological activity of the compounds.

It is believed that the present compounds employ the oligopeptide transporters for delivery to the deeper tissues of the cornea, unlike ACV and GCV, which have poor ocular bioavailability. Thus, they are effective in cases where the corneal stromal and underlying tissues have been infected. They have shown excellent in vitro antiviral activity against HSV 1 in HFF cells and in vivo rabbit epithelial keratitis with no significant cytotoxicity.

Thus, the present compounds provide a significant therapeutic advantage over the current therapy for HSV keratitis, which uses highly cytotoxic trifluorothymidine (TFT). These peptide derivatives of ACV exhibit high aqueous solubility and good stability at pH 5.6 showing no measurable degradation in 7 days. This is in contrast to valcyclovir, which is not stable in solution. This stability will permit the preparation of stable aqueous formulations of pH 5.0-6.0 and up to about 20 mg/ml concentration of the compounds of the invention. ACV, on the other hand, has a saturable solubility of only 2 mg/ml at 37° C. As exemplified hereinbelow, the dipeptide ACV derivative Val-Val-ACV also has excellent in vivo activity against rabbit stromal keratitis, which is not adequately treated by current antiviral therapeutic regimens. Therefore, Val-Val-ACV can be used in topical antiviral formulations, such as liquid eye drops or eye washes for ocular instillation.

The dipeptide esters of ACV exemplified hereinbelow are also found to be less toxic than trifluorothymidine and ACV.

DETAILED DESCRIPTION OF THE INVENTION

Figure 1:
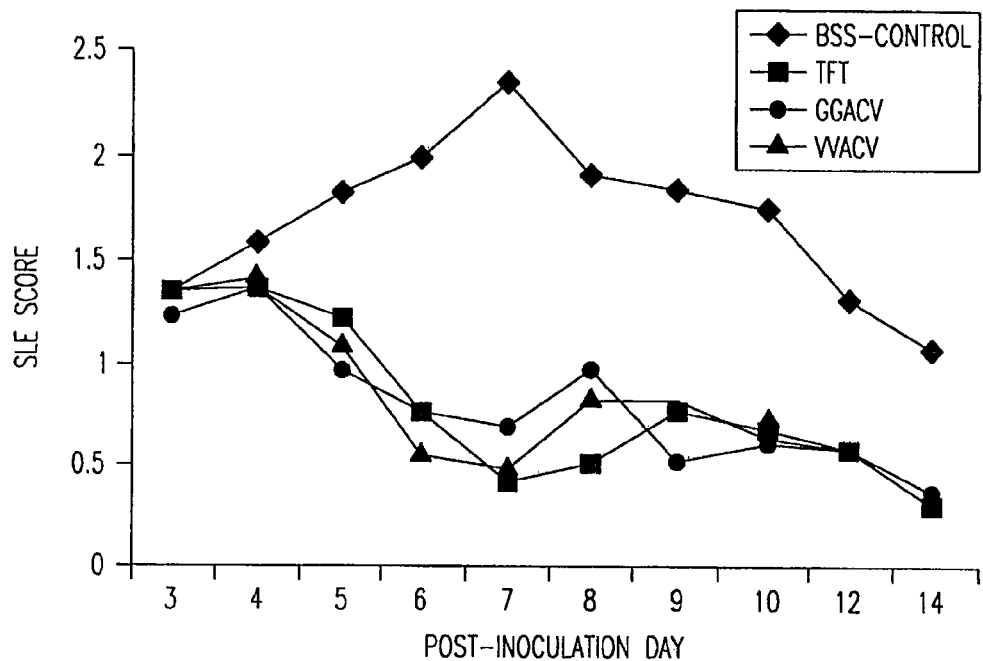
FIG. 1 is a graph depicting SLE scores for Gly-Gly-ACV and Val-Val-ACV in an HSV-1 epithelial keratitis model.

The following definitions are used, unless otherwise described: Alkyl denotes both straight and branched groups; but reference to an individual radical such as "propyl" embraces only the straight chain radical, a branched chain isomer such as "isopropyl" being specifically referred to.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val). The terms "amino acid" and particular amino acids (e.g. Met, Val, Thr, Tyr, Trp, Ser, Ala, or Gly) include amino acid residues and include both the D and L stereoisomeric forms.

The term "herpes virus" includes any virus of the herpes virus family, e.g., herpes simplex virus 1 (HSV-1), herpes simplex virus 2 (HSV-2), varicella zoster virus (VZV), epstein-barr virus (EBV), and human cytomegalovirus (HCMV).

The abbreviation "ACV" refers to acyclovir. The abbreviation "GCV" refers to ganciclovir. Amino acids are referred to by their standard three-letter abbreviations. Peptide sequences are written left to right from the amino to the carboxy terminus. Peptide esters of acyclovir wherein the hydroxyethoxymethyl group is esterified are referred to herein by abbreviations such as "Gly-Val-ACV." This is a compound of formula (I) in which the carboxy group of the Valine residue of the Gly-Val dipeptide is esterified to the hydroxy group of acyclovir to form the R$^4$ group of a compound of formula (I) as shown below.

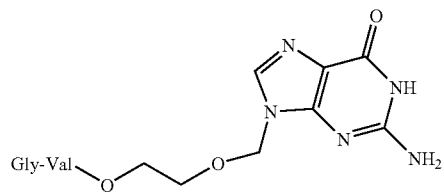

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-viral activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, (C$_1$-C$_4$)alkyl can be methyl, ethyl, propyl, isopropyl, butyl, iso-butyl, or sec-butyl; (C$_3$-C$_6$)cycloalkyl can be cyclopropyl, cyclobutyl, cyclopentyl, or cyclohexyl; hydroxy(C$_1$-C$_4$)alkyl can be hydroxymethyl, hydroxyethyl, 3-hydroxypropyl, 2-hydroxypropyl, or 4-hydroxybutyl.

In one embodiment, a compound of the invention is a compound of formula (II):

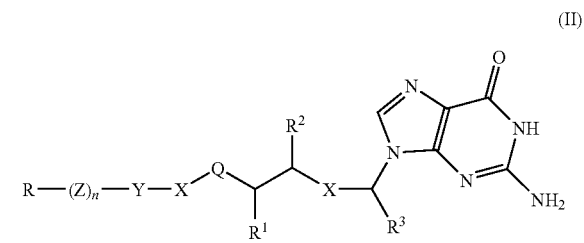

wherein R is H or an amino-protecting group; n is 0 or 1; R$^1$ is H, (C$_1$-C$_4$)alkyl, (C$_3$-C$_6$)cycloalkyl, (C$_4$-C$_7$)cycloalkylalkyl, hydroxy(C$_1$-C$_4$)alkyl, benzoyl(C$_1$-C$_4$)alkyl or phenyl;

$R^2$ is H, OH or ($C_1$-$C_4$)alkyl; $R^3$ is H, ($C_1$-$C_4$)alkyl or hydroxy ($C_1$-$C_4$)alkyl; Q is O or S; and X, Y and Z are individually, Met, Val, Thr, Tyr, Trp, Ser, Ala, or Gly; or a pharmaceutically acceptable salt thereof.

In a particular embodiment of the compounds of formula (I) or (II), each Q is O.

In a particular embodiment of the compounds of the invention, each Y and X is individually Gly or Val.

In a particular embodiment of the compounds of the invention, R is H, acetyl, or t-butoxycarbonyl.

In a particular embodiment of the compounds of the invention, each R is H.

Preferably, in the compounds of formula (I) and formula (II) at least 1, 2 or 3 of $R^1$, $R^2$ and $R^3$ are H.

In a particular embodiment of the compounds of the invention, each n is 0.

In a particular embodiment of the compounds of the invention, Y—X or $(Z)_n$-Y—X is Val-Val, Gly-Gly, Val-Gly or Gly-Val, most preferably Val-Val or Gly-Gly.

In a particular embodiment, the amino acid residues in the compounds of the invention are the L stereoisomers.

In a particular embodiment of the invention, the compound of formula (I) is a compound of formula (III):

(III)

Y—X—O structure with guanine derivative wherein X—Y— is Val-Val-, Val-Gly-, Gly-Val-, or Gly-Gly-.

In a particular embodiment of the compound of formula (III), Y—X is Val-Val- or Gly-Gly-.

In a particular embodiment of the invention, the compound of formula (I) is a compound of formula (IV):

(IV)

Y—X—O structure with CH$_2$ and Y—X—O branch, guanine derivative

In a particular embodiment of a compound of formula (I), $R^2$ is CH$_2$OH and $R^4$ is $R^a$.

In another particular embodiment of a compound of formula (I), $R^2$ is CH$_2R^a$ and $R^4$ is $R^a$. In this embodiment, the $R^a$'s of $R^2$ and $R^4$ can be the same or different from each other.

In another particular embodiment of the compound of formula (I), $R^2$ is CH$_2R^a$ and $R^4$ is OH.

In the embodiments where $R^2$ is CH$_2$OH and $R^4$ is $R^a$, or $R^2$ is CH$_2R^a$ and $R^4$ is $R^a$, or $R^2$ is CH$_2R^a$ and $R^4$ is OH, X—Y of $R^a$ in some embodiments is Val-Val, Gly-Gly, Val-Gly, or Gly-Val.

It has been discovered that linking a therapeutic agent to one or more groups of the formula —X—Y-$Z_{(n)}$-R facilitates the agent for targeted delivery into the ocular tissues. In the formula —X—Y-$Z_{(n)}$-R, the tick mark on X indicates the point of attachment to the therapeutic agent. Each X, Y and Z is independently Met, Val, Thr, Tyr, Trp, Ser, Ala or Gly; each R is independently H or an amino-protecting group; and each n is independently 0 or 1. Preferably, X is linked to the therapeutic agent through the α-carbonyl group of the amino acid that is X. The group —X—Y-$Z_{(n)}$-R can be linked to the therapeutic agent at any synthetically feasible position, e.g., to a hydroxyl, mercapto, or amino group on the therapeutic agent to form an ester, ether, thioether, thioester, or amide linkage to —X—Y-$Z_{(n)}$-R.

Accordingly, the invention also provides a therapeutic agent linked to one or more groups of the formula —X—Y-$Z_{(n)}$-R; wherein each X, Y and Z is independently Met, Val, Thr, Tyr, Trp, Ser, Ala or Gly; each R is independently H or an amino-protecting group; and each n is independently 0 or 1.

The therapeutic agents that can be linked to one or more groups of the formula —X—Y-$Z_{(n)}$-R for targeted delivery to the ocular tissues include antibiotics, antiglaucoma agents, anticancer agents, and anti-inflammatory agents.

Examples of antibiotics suitable for use in the present invention include, but are not limited to, 4-sulfanilamidosalicylic acid, acediasulfone, amfenac, amoxicillin, ampicillin, aztreonam, bambermycin(s), carbenicillin, carumonam, cefamandole, cefatrizine, cefixime, cefmenoxime, cefminox, cefodizime, cefonicid, cefoperazone, cefotaxime, cefpimizole, cefpiramide, cefpirome, cefprozil, cefroxadine, ceftazidime, cefuzonam, cephalexin, cephaloglycin, cephalosporin C, ciprofloxacin, clinafloxacin, cyclacillin, enoxacin, epicillin, flomoxef, imipenem, moxalactam, mupirocin, nadifloxacin, neomycin, norfloxacin, panipenem, pazufloxacin, penicillin N, pipemidic acid, polymixin, quinacillin, ritipenem, salazosulfadimidine, sparfloxacin, succisulfone, sulfaloxic acid, temocillin, ticarcillin, tigemonam, tosufloxacin, trovafloxacin, vancomycin, and the like.

Examples of anti-glaucoma agents suitable for use in the present invention include, but are not limited to, betaxolol, timolol maleate, dichlorphenamide, demecarium, and phenylephrine.

Examples of anti-cancer agents suitable for use in the present invention include, but are not limited to 6-diazo-5-oxo-L-norleucine, azaserine, carzinophillin A, denopterin, edatrexate, eflornithine, melphalan, methotrexate, mycophenolic acid, podophyllinic acid 2-ethylhydrazide, pteropterin, streptonigrin, tamoxifen, Tomudex® (N-((5-(((1,4-Dihydro-2-methyl-4-oxo-6-quinazolinyl)methyl)methylamino)-2-thienyl)carbonyl)-L-glutamic acid), ubenimex, and the like.

Examples of anti-inflammatory compounds suitable for use in the present invention include, but are not limited to aspirin, 3-amino-4-hydroxybutyric acid, aceclofenac, alminoprofen, bromfenac, bumadizon, carprofen, dexamethasone, diclofenac, diflunisal, enfenamic acid, etodolac, fendosal, flufenamic acid, gentisic acid, hydrocortisone, lodoxamide, lodoxamide tremathamine, meclofenamic acid, mefenamic acid, mesalamine, niflumic acid, olsalazine oxaceprol, predinsolone, S-adenosylmethionine, salicylic acid, salsalate, sulfacetamide, sulfasalazine, sulindac, tolfenamic acid, and the like.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art. For example, salts of the enol form of the compound of formula (I) may be prepared in the usual manner by reacting the keto form with one or more equivalents of a desired base such as, for example, a metallic hydroxide base, e.g., sodium hydroxide; a metal carbonate or bicarbonate base such as, for example, sodium carbonate or sodium bicarbonate.

Acid addition salts of the present compounds may be prepared by reacting the present compounds with one or more equivalents of the desired inorganic or organic acid, such as, for example, hydrochloric acid. Esters, ketals and acetals of hydroxyl groups of the compounds may also be prepared by any of the usual methods known in the art for esterifying or protecting OH groups.

Processes for preparing compounds of formula I are provided as further embodiments of the invention and are illustrated by the procedures described in the Examples. Specifically, the compounds of formulas (I)-(IV) can be prepared from convenient starting materials, employing procedures (e.g., reagents and reaction conditions) known to those of skill in the art. For example, suitable reagents and reaction conditions are disclosed, e.g, in *Advanced Organic Chemistry, Part B: Reactions and Synthesis*, Second Edition, Cary and Sundberg (1983); *Advanced Organic Chemistry, Reactions, Mechanisms, and Structure*, Second Edition, March (1977).

Amino-protecting groups, R, are available to the art of polypeptide synthesis, and include ($C_2$-$C_4$)acyl, i.e., acetyl, benzyl, carbobenzyloxy (CBZ), t-butylcarbobenzoxyl (t-Boc), benzoyl, and the like. *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999). N-acyl derivatives of amino groups of the present peptide moieties may be prepared by utilizing an N-acyl protected amino acid for the final condensation, or by acylating a protected or unprotected peptide. O-acyl derivatives may be prepared, for example, by acylation of a free hydroxy peptide. Either acylation may be carried out using standard acylating reagents such as acyl halides, anhydrides, acyl imidazoles, and the like. Both N- and O-acylation may be carried out together, if desired.

Methods to test compounds of the invention for desired properties or biological activity are known to persons of skill in the art. For instance, methods to test for anti-herpes virus activity, for hydrophilicity, or for uptake into a desired tissue, such as the aqueous humor or vitreous humor of the eye, are provided in the Examples below.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders, for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. They may also be administered to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The present compounds can also be delivered from controlled release intraocular devices such as contact lens-type inserts, other ocular inserts, and polymeric patches and bandages. Dosing can be determined empirically by the treating physician based on the known $IC_{50}$'s of ACV against herpes viruses, or extrapolated from the in vivo and in vitro studies conducted hereinabove. Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%.

Preferably, the compositions are adapted for topical administration, such as to the eye, and an opthalmologically acceptable vehicle such as an aqueous vehicle, a gel or an ointment is employed. Such vehicles can be buffered to about pH 5-6 and can also contain preservatives, thickeners and solubilizing agents as needed. Preferably, the compositions are formulated as eyedrops, and can contain up to about 10-100 mg/ml of the present compound(s). Exemplary liquid eye drop compositions contain 0.1% sodium hyaluronate (average molecular weight 1,800,000) or 0.1% Polysorbate 80 by weight to volume in water. The liquid compositions also may contain buffers, isotonic salts, and preservatives such as EDTA and thimerosal. The active compounds of the invention may be, for instance, diluted into an eye drop composition from a liquid composition containing ethanol, to give a final composition containing ethanol at low concentrations, e.g., 1% or less.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg.

The compound is conveniently administered in unit dosage form; for example, containing 5 to 1000 mg of active ingredient per unit dosage form.

Ideally, the active ingredient should be administered to achieve peak plasma concentrations of the active compound of from about 0.5 to about 75 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds of the invention can also be administered in combination with other therapeutic agents that are effective antiviral agents or effective to treat or alleviate the symptoms of HSV keratitis. For instance, the compounds of the invention can be administered in combination with 5'-iododeoxyuridine, trifluorothymidine or acyclovir.

Acyclovir derivatives wherein $R^1$, $R^2$ and $R^3$ are not H and/or X is S can be prepared as disclosed in U.S. Pat. No. 4,199,574.

The present dipeptide and tripeptide esters of ACV and GCV can be synthesized by the general procedures of Beauchamp et al. (L. M. Beauchamp et al., *Antiviral Chem. Chemotherap.*, 3, 157 (1992)). $^1$HNMR spectra were measured at 250 MHz (Bruker AC 250).

The invention will now be illustrated by the following non-limiting Examples.

Example 1

Preparation of Val-Val-Acv

The synthesis of compound 5 was carried out as summarized in Scheme 1, below.

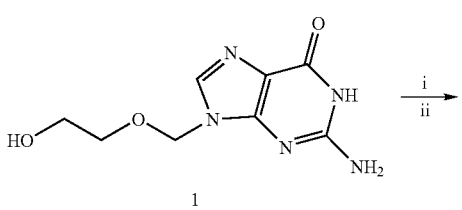

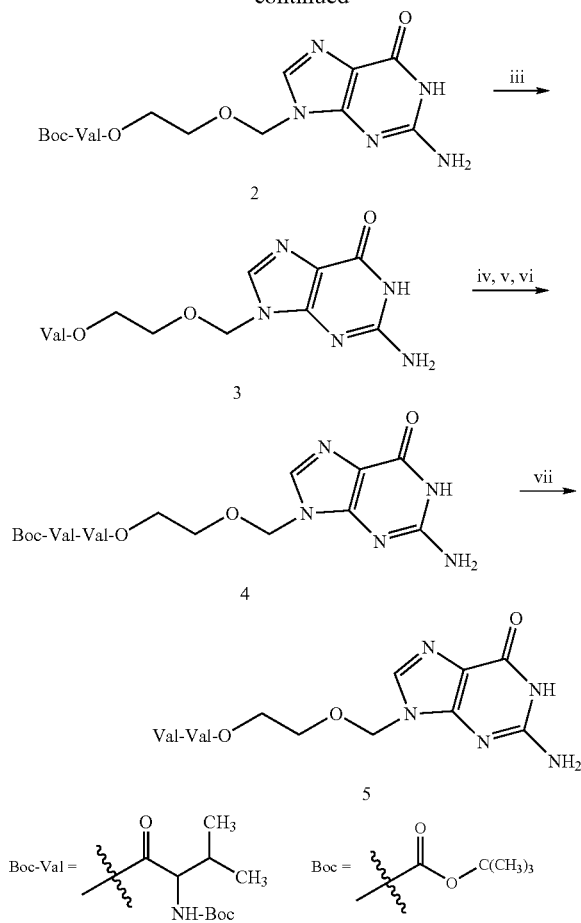

i) Boc-VAL, DCC, DMF, 0° C., 1 hr, ii) DMAP, DMF, 18 hrs, rt iii) TFA, 0° C., 30 min, iv) Boc-Val, DCC, DMF, 0° C., 1 hr, v) TEA, rt, vi) adding Boc-Val amino acid anhydride (step iv) to the neutralized Val-ACV (step v), 5 hrs, rt, vii) TFA, 0° C., 30 min.

Synthesis of the Val-Val-ACV ester of acyclovir involves (i) formation of Boc-Val amino acid anhydrides, ii) coupling of the Boc-Val anhydride with ACV (1), iii) deprotecting the Boc-Val-ACV, iv) formation of Boc-Val anhydrides, v) neutralizing of Val-ACV, vi) coupling of the Boc-Val acid anhydride with the neutralized Val-ACV (formation of dipeptide), and vii) finally deprotection of the amino group of Boc-Val-Val-ACV.

A mixture of Boc-Val and dicyclohexyl carbodiimide (DCC) in dimethylformamide (DMF) in a ratio of 1:2 DCC/Boc-Val was stirred for 1 hr at 0° C. under nitrogen atmosphere. A solution of acyclovir (1) and 4-N,N(dimethylamino)pyridine (DMAP) was added to the reaction mixture, stirred for 18 hrs and then filtered. The solvent of the filtrate was partially removed in vacuo and the impure solution was added dropwise to cold diethyl ether. The resulting precipitate (2) was filtered and dried, followed by acidolytic removal (treating Boc-Val-ACV with trifluoroacetic acid (TFA) for 30 min at 0° C.) of the Boc protecting group to yield Val-ACV (3). Compound (3) was neutralized by triethylamine (TEA) and treated with the amino acid anhydride of Boc-Val for about 5 hrs. The solvent was removed from the reaction mixture in vacuo and the reaction mixture was added dropwise to the cold diethyl ether. The resulting precipitate (4) was filtered, dried and the Boc group was deprotected (acidolytic removal) to yield the desired dipeptide ester of acyclovir Val-Val-ACV (5).

Val-Val-ACV: MS [M+1]$^+$=423.7, H$^1$NMR (DMSO-d$_6$+ TMS) δ 0.88 (s, 12H, CH$_3$), 2.00 (s, 2H, CH(CH$_3$)$_2$), 3.68 (s, 3H, H-3', H$_2$NCHCO), 4.14 (s, 3H, CH$_2$OC(O), CHCOO), 5.35 (s, 2H, H-1'), 6.69 (brs, 4H, NH$_2$), 7.94 (NH$_2{}^+$), 8.14 (s, 1H, H-8), 8.57 (brs, NH$_3{}^+$), 10.89 (brs, 1H, CONH).

Example 2

Preparation of Gly-Gly-ACV (3)

The availability of carbobenzyloxy(CBZ)-Gly-Gly reduced the steps of the synthesis to only three, two of which are similar to the corresponding steps of Scheme 1. The difference in the third step lies in the cleavage of CBZ protecting group. For the deprotection, a solution of (2) in MeOH, tetrahydrofuran (THF), water was added to 0.5N aqueous HCl and 10% Pd/C. The mixture was shaken in a Parr apparatus under an initial pressure of 50 psi of hydrogen at ambient temperature for 60 hrs. The mixture was filtered, the catalyst was washed with MeOH, and the combined washings and filtrate were lyophilized. The residue was recrystallized following the method reported by Beauchamp et al., cited above.

Scheme 2

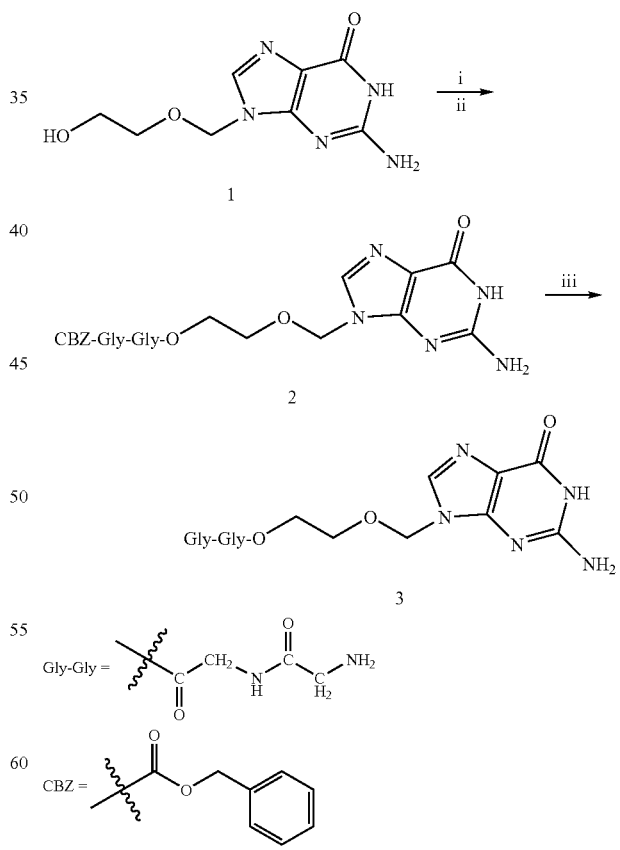

i) CBZ-Gly-Gly, DCC, DMF, 0° C., 1 hr, ii) DMAP, DMF, 18 hrs, rt, iii) MeOH, THF, H$_2$O, 0.5HCl, 10% Pd/C, 60 hrs.

A mixture of CBZ-Gly-Gly and dicyclohexyl carbodiimide (DCC) in dimethylformamide (DMF) in a ratio of 1:2 CBZ-Gly-Gly:DCC was stirred for 1 hr at 0 EC under nitrogen atmosphere. A solution of acyclovir (1) and 4-N,N(dimethylamino)pyridine (DMAP) was added to the reaction mixture, stirred for 18 hrs and then filtered. The solvent of the filtrate was partially removed in vacuo and the impure solution was added dropwise to cold diethyl ether. A solution of CBZ-Gly-Gly-ACV in methanol, tetrahydrofuran (THF) and water was added to 0.5 N aqueous HCl and 5% palladium on charcoal. The mixture was shaken in a Parr apparatus under a pressure of 50 psi of hydrogen at room temperature for about 40 hours. The mixture was filtered and the filtrate was evaporated under vacuum at 501 C.

Gly-Gly-ACV: MS $[M+1]^+=339.7$, $H^1$NMR (DMSO-$d_6$+ TMS) δ 3.15 (s, 1H, NH), 3.59 (s, 2H, $CH_2COQ$), 3.65 (s, 2H, $CH_2O$), 3.92 (d, 2H, $NH_2CH_2$), 4.14 (brs, 2H, $CH_2OC(O)$), 5.35 (s, 2H, H-1'), 6.65 (s, 4H, $2NH_2$), 7.82 (s, 1H, H-8), 8.82 ($NH_3^+$).

Example 3

Preparation of Other Amino Acid and Dipeptide Esters of Acyclovir

ACV was synthesized as reported in Izawa, K., et al., *Pure Appl. Chem.* 70:313 (1998); and Shiragama, K. et al., *Nucleosides Nucleotides* 14:337 (1995). The amino acid and peptide esters were formed as in Example 1, by i) formation of N-protected amino acid anhydrides, ii) coupling of the N-protected amino acid anhydride with ACV, iii) deprotecting the amino group of the amino acid ester of ACV, iv) formation of the second N-protected amino acid anhydride, v) coupling of the N-protected amino acid anhydride with the deprotected amino acid esters of ACV (formation of the dipeptide ester), and vii) finally deprotection of the amino group of the dipeptide ester of ACV. By this method, Gly-Val-ACV, Tyr-Val-ACV, Val-Tyr-ACV, Tyr-Gly-ACV, and Gly-Tyr-ACV were synthesized.

Example 4

Analytical Procedure

HPLC methods for the present derivatives of ACV have been developed. The chromatographic conditions for the derivatives are summarized in Table 1.

TABLE 1

HPLC Assay conditions and retention times for the esters

| Compound | Composition of aqueous Phase (pH = 2.5) | Composition of organic Phase | Mobile Phase Aq:Org | Retention Times (min.)[a] | | |
|---|---|---|---|---|---|---|
| | | | | Parent Drug | Amino Acid Ester | Dipeptide Ester |
| Val-Val-ACV | 25 mM $NH_4H_2PO_4$ | Acetonitrile | 92:7 | 3.2 | 5.5 | 13.8 |
| Gly-Gly-ACV | 25 mM $KH_2PO_4$ | Acetonitrile | 98:2 | 8.8 | 7.0 | 10.8 |
| Val-ACV | 25 mM $NH_4H_2PO_4$ | Acetonitrile | 95:5 | 5.2 | 8.0 | — |
| Gly-Val-ACV | 25 mM $NH_4H_2PO_4$ | Acetonitrile | 95:5 | 5.2 | 8.0 | 20.1 |
| Tyr-Val-ACV | 25 mM $NH_4H_2PO_4$ | Acetonitrile | 94:6 | 3.9 | 5.5 | 15.6 |
| Val-Tyr-ACV | 25 mM $NH_4H_2PO_4$ | Acetonitrile | 94:6 | 3.9 | 5.5 | 30.1 |
| Tyr-Gly-ACV | 25 mM $NH_4H_2PO_4$ | Acetonitrile | 95:5 | 5.2 | 4.1 | 15.2 |
| Gly-Tyr-ACV | 25 mM $NH_4H_2PO_4$ | Acetonitrile | 95.5 | 5.2 | 10.3 | 22.1 |
| ACV | 25 mM $NH_4H_2PO_4$ | Acetonitrile | 98:2 | 8.8 | — | — |
| Gly-Gly-ACV | 25 mM $NH_4H_2PO_4$ | Acetonitrile | 98:2 | 8.8 | 7.0 | 10.8 |

[a]UV detection at $\lambda_{max}$ = 254 nm.

Example 5

Physicochemical Properties of ACV Dipeptide Ester Derivatives

Aqueous stability studies were carried out over a pH range of 1.2-9.0. The first order hydrolytic rate constants obtained have been summarized in Table 2. The data shows that Val-Val-ACV and Gly-Gly-ACV will be stable for two years as an ophthalmic solution at pH 5.6.

TABLE 2

Aqueous Stability data of dipeptide derivatives of ACV as a function of pH

| | pH: | | | | | |
|---|---|---|---|---|---|---|
| | 1.2 | 2.6 | 4.2 | 5.6 | 7.4 | 9.0 |
| Val-ACV | 1.22 | 0.41 | 0.008 | 0.16 | 0.67 | 1.63 |
| Val-Val-ACV | 0.0062 | 0.0051 | * | * | 0.107 | 0.24 |
| Gly-Gly-ACV | * | ND | * | * | 6.75 | 14.85 |

Values are k × $10^3$ $min^{-1}$
* No measurable degradation during the course of 7 day experiment.
ND—Not determined.

Example 6

Estimation of Cell Cytotoxicity Using Cell Proliferation Assay

Studies were carried out to examine comparative toxicities of TFT, ACV and the dipeptide derivatives (Gly-Gly-ACV and Val-Val-ACV) in a rabbit corneal cell line (SIRC). For this assay, CellTiter 96® $AQ_{ueous}$ Non-Radioactive Cell Proliferation Assay Kit (Promega, Madison, Wis. was used. This assay is a colorimetric method for determining the number of cells in proliferation.

SIRC cells (passage 410-425) were plated in 96 well plates. Solutions of TFT and the various ACV derivatives (10 μM-10 mM) were made in the culture medium and appropriate volumes were added to make up to a final volume of 100 μl medium in each well. A plate was seeded for each time point (24 hr, 48 hr and 72 hr). The cells were incubated along with the drug solution in a humidified 5% $CO_2$ atmosphere. The effect of the compounds on the proliferation of these cells was observed as a function of drug concentration and the time of exposure. The proliferation of SIRC cells in the presence of different concentrations of TFT and the compounds was compared with the positive control (without drug) at each time point and these values were all corrected for, using a negative control (without cells).

As shown in Table 3, TFT inhibited cell growth in a concentration dependent manner. ACV also inhibited growth but to a much lesser extent. TFT caused complete cell death (0.01% viable) at and above 5 mM. The inhibitory effect was found to be time dependent. Experiments were performed up to 96 hrs with all the compounds. The two dipeptide derivatives of ACV were also screened for cytotoxicity and showed no inhibition up to 2 mM concentrations and no appreciable toxicity was found up to 48 hr.

TABLE 3

Cell cytotoxicity using cell proliferation assay

| Conc (mM) | TFT | ACV | Gly-Gly-ACV | Val-Val-ACV |
|---|---|---|---|---|
| 0 | 100 | 100 | 100 | 100 |
| 0.025 | 86.98 | 94.71 | ND | ND |
| 0.25 | ND | ND | 104.6 | 86.3 |
| 0.1 | 80.48 | 89.41 | ND | ND |
| 0.5 | 64.76 | 69.81 | 94.7 | 85.8 |
| 1 | 54.35 | 57.37 | 90.1 | 87.0 |
| 2 | ND | ND | 86.2 | 87.0 |
| 5 | 0.01 | 49.12 | 63.8 | 99.3 |
| 10 | ND | ND | 49.32 | 54.03 |

ND—not determined
Values are percent survival

Example 7

In Vitro Antiviral Screening Against Herpes Group Viruses

The in vitro potency of selected dipeptide derivatives, namely Gly-Gly-ACV and Val-Val-ACV were determined against various Herpes viruses. The compounds were screened against HSV-1, HSV-2, EBV, VZV and HCMV. Low passage human fibroblast foreskin cells (HFF) were used at a concentration of $2.5 \times 10^6$ cells per ml in 0.1 ml of minimum essential medium (MEM) supplemented with 10% fetal bovine serum.

For HSV-1 and HSV-2, 1000 plaque forming units (PFU) per well were used. CMV, VZV and EBV were used at a concentration of 2500 PFU per well.

It was found that the test compounds were particularly effective against HSV-1 and the antiviral efficacies were comparable with ACV.

Example 8

In Vivo Antiviral Efficacy Studies in HSV-1 Rabbit Keratitis Model

The rabbit eye is an excellent model to study acute HSV-1 epithelial keratitis. Also, spontaneous and induced ocular HSV-1 shedding and corneal epithelial disease in rabbits has been used as a model of human ocular HSV-1 reactivation and recurrence. HSV-1 strain McKrae was used in studies for epithelial keratitis. HSV-1 strain RE was used for studies of HSV stromal keratitis. The Ocular Lesion Scoring System is given in Table 4.

TABLE 4

Ocular Lesion Scores for HSV-1 Infection in Rabbit and Mouse Eyes

| SLE Scores | Characteristics |
|---|---|
| A. Corneal epithelium: | |
| 0.0-0.5 | Normal to non-specific, random superficial lesion |
| 0.6-0.9 | Punctate ulcerations; specific and deep |
| 1.0-1.9 | One or more dendritic ulceration |
| 2.0-2.9 | Geographic ulceration or trophic erosion (less than 50% of cornea involved) |
| 3.0-4.0 | Geographic ulceration or trophic erosion (more than 50% of cornea involved) |
| B. Stroma: | |
| 0.0 | Normal |
| 0.5-0.9 | Mild edema; not diffuse; no haze |
| 1.0-1.9 | Significant edema; slight haze; iris clearly visible |
| 2.0-2.9 | Gross edema; stroma swelling; cloudy, diffuse, can see anterior chamber; iris visible |
| 3.0 | Severe stromal edema; very cloudy, cannot see anterior chamber; pupillary border no longer distinct |
| 4.0 | Opaque cornea, anterior chamber structure not visible. Add 1.0 if descemetocele formation, perforation, or corneal vascularization present. | i) Epithelial Keratitis: A group of ten rabbits was used to study each compound. Both eyes of all rabbits were used. An aqueous vehicle (like a placebo) and one positive control were obtained using 1% TFT (Viroptic®). Each compound at 1% concentration (TFT=33 mM, Gly-Gly-ACV=26.6 mM, Val-Val-ACV=18.6 mM) were applied (50 μl) topically 5 times per day every two hours starting at 8:00 a.m. and ending at 4:00 p.m. The treatment began on the $3^{rd}$ post-inoculation day and continued for 5 consecutive days. Slit-lamp examinations were performed once every day for 8 days and thereafter once every other day until lesions resolved. The slit-lamp scoring system for HSV-1 McKrae in rabbit and mouse eyes has been summarized in Table 4. The ACV derivatives (Gly-Gly-ACV and Val-Val-ACV) are more effective than TFT with Trp-ACV being twice as effective (FIG. 1, Table 5).

TABLE 5

Concentrations required to achieve an SLE Score of 0.3 in epithelial keratitis rabbit model after 14 days post-inoculation

| Compound | Conc (mM) |
|---|---|
| TFT | 33.3 mM |
| Gly-Gly-ACV | 26.6 mM |
| Val-Val-ACV | 18.6 mM | ii) Stromal Keratitis: The experiment is similar to the part (i) experiment as far as the treatment cycles for all experimental drugs (TFT and Val-Val-ACV) are concerned. The effect of Val-Val-ACV on stromal keratitis induced by intrastromal injection with a high (20 μl of a $1 \times 10^7$ pfu/ml stock) titer of HSV-1RE strain was compared to that of TFT. Each compound at 1% concentration (TFT=33 mM, Val-Val-ACV=18.6 mM) was applied topically. The same scoring as noted in Table 4 is used for stromal keratitis. Emphasis is placed on the stromal edema and visibility into the aqueous chamber and the visualization of the pupil and iris.

Figure 2:
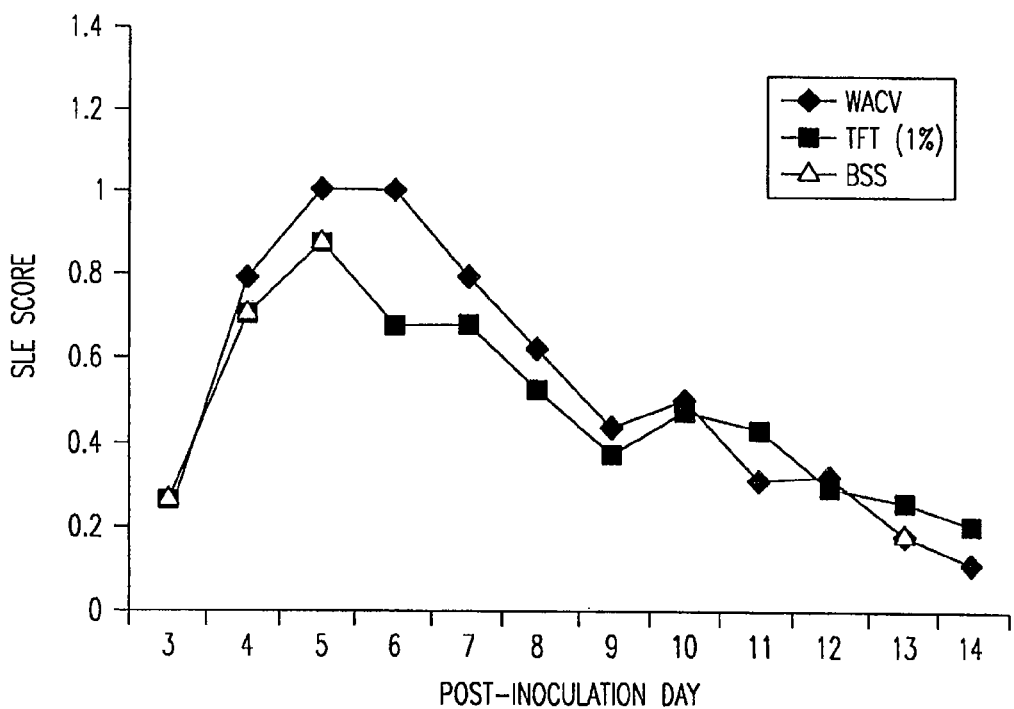
FIG. 2 is a graph depicting SLE scores for Val-Val-ACV in an HSV-1 stromal keratitis model.

A group of ten rabbits were used to study each compound. Both eyes of all rabbits were treated. Three to four groups of 10 rabbits are used in one experiment. This includes vehicle control, TFT, and the newly synthesized antiviral Val-Val-ACV. The above studies indicated that Val-Val-ACV is twice as effective as TFT (FIG. 2, Table 6).

TABLE 6

Concentrations required to achieve an SLE Score of 0.2 in stromal keratitis rabbit model after 13 days post-inoculation

| Compound | Conc (mM) |
|---|---|
| TFT | 33.3 mM |
| Val-Val-ACV | 18.6 mM |

Example 9

Ocular Tissue Hydrolysis

Figure 3A:
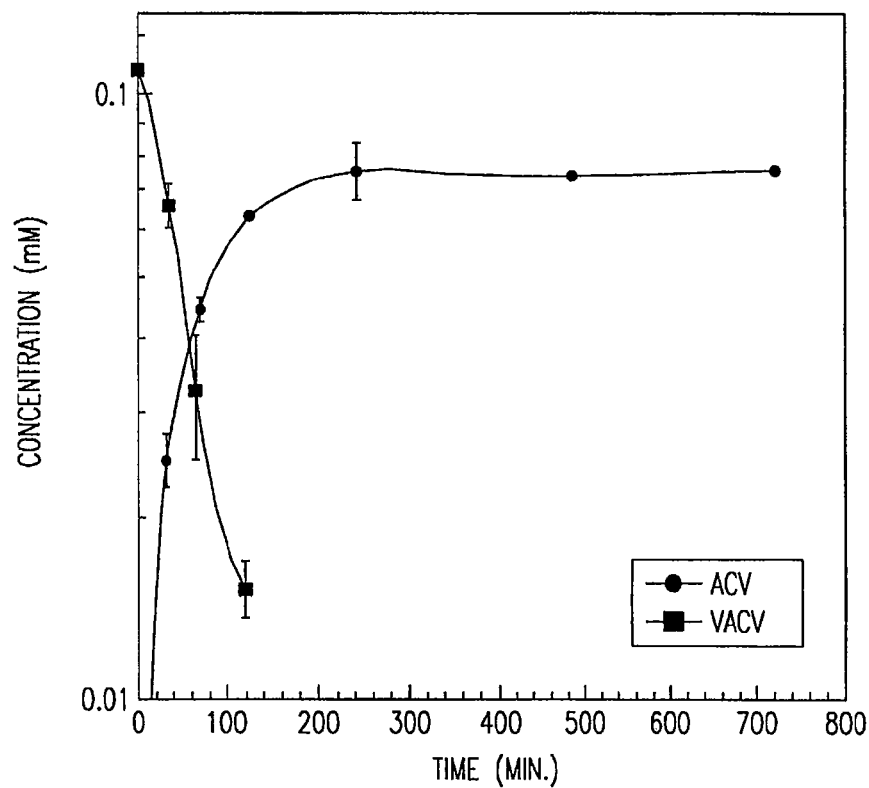
FIG. 3 is a graph of the time course of regeneration of ACV from L-Val-ACV (panel A) or Val-Val-ACV (panel B) upon enzymatic hydrolysis in corneal tissue homogenate. (Mean±S.D., n=3.)
Figure 3B:
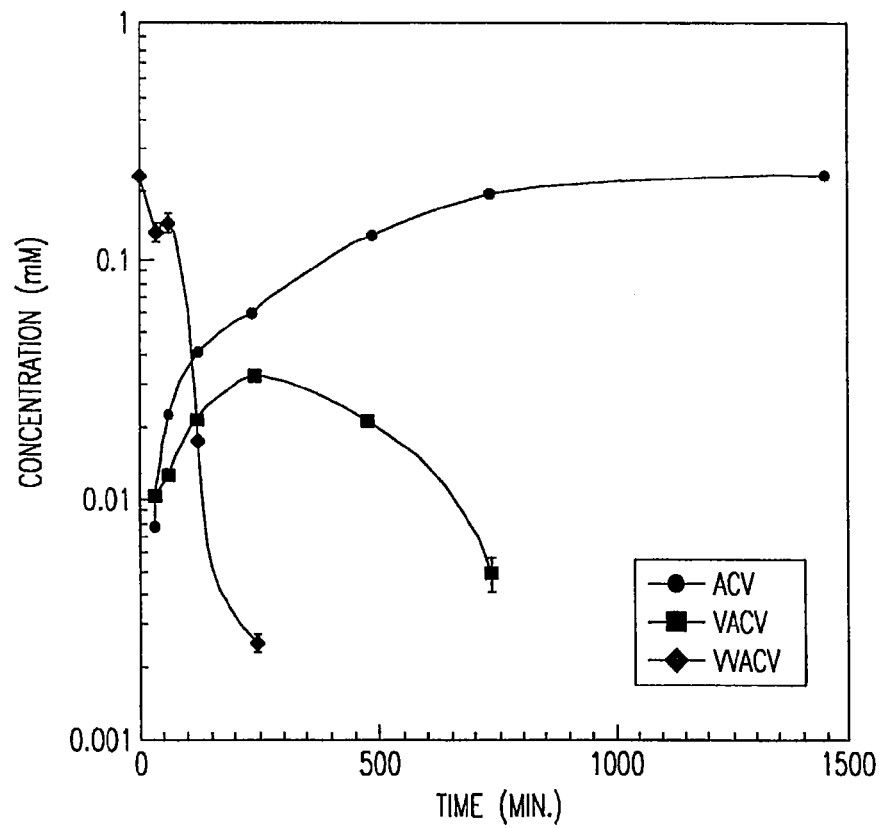

Release of ACV from Val-Val-ACV upon subsequent hydrolysis to Val-ACV in isolated rabbit cornea was observed (FIG. 3), indicating that these derivatives cleave to yield ACV which is responsible for the activity in vivo and in vitro. It is believed that Val-Val-ACV is sequentially hydrolyzed via Val-ACV by dipeptidases and aminopeptidases in ocular tissues and fluids to yield the parent drug ACV. The hydrolysis is mainly enzymatic and not chemical as Val-Val-ACV is relatively more stable in IPBS (pH 7.4, $t_{1/2}$=108 hrs).

Example 10

Interactions of the Dipeptide Ester Derivatives of Acyclovir with the Intestinal Oligopeptide Transporter Competitive Inhibition of Glycylsarcosine Transport in the Human Intestinal Cell Line Caco-2

The human peptide transporter, hPEPT1 displays broad substrate specificity and recognizes dipeptides and tripeptides, but not free amino acids, as its primary substrates. The peptide transporter not only carries nutrients across absorptive cell membranes but also functions in the transport of exogenous compounds that have peptide like structures. Small dipeptides, ACE inhibitors, β-Lactam antibiotics are known substrates for intestinal PEPT1.

A series of novel water-soluble dipeptide ester derivatives of acyclovir were thus synthesized in order to target the peptide transporter on the cornea and intestinal epithelial cells for improved ocular and oral bioavailability of acyclovir respectively. In this Example we discuss the application of these derivatives for improved oral bioavailability by assessing their hydrolysis and affinity towards hPEPT1 using the well characterized human intestinal Caco-2 cell line (Hidalgo et al., 1989). Caco-2 cells have been shown to express the human di/tripeptide transporter, hPEPT1 and have been used to characterize various peptidomimetics and other substrates that are recognized by the peptide transporter (Nielsen et al., 2001). The affinities of these ACV derivatives towards the hPEPT1 transporter present on Caco-2 cells were determined. The transport characteristics of one of the dipeptide esters, Gly-Val-ACV (Gly-Val-ACV) across Caco-2 monolayer were compared to that of Val-ACV in order to establish whether these compounds may be transported across cell membranes owing to their recognition by the peptide transporter.

Materials and Methods

Materials: [$^3$H] Glycylsarcosine (Gly-Sar; 4 Ci/mmol) was purchased from Moravek Biochemicals (Brea, Calif.) and [$^{14}$C] Mannitol (50 mCi/mmol) was supplied by Amersham (Piscataway, N.J.). Human colon carcinoma derived Caco-2 cells were obtained from American Type Culture Collection (ATCC, Rockville, Md.). The growth medium, Dulbecco's modified Eagle Medium was obtained from Life Technologies (Grand Island, N.Y.). MEM non-essential amino acids (NEAA), penicillin, streptomycin, sodium bicarbonate, HEPES, unlabeled glycylsarcosine (Gly-Sar) and cephalexin were purchased from Sigma Chemical Company (St. Louis, Mo.). Fetal bovine serum (FBS) was purchased from JRH Biosciences (Lenexa, Kans.). Culture flasks (75 cm$^2$ growth area), polyester Transwells® (pore size 0.4 µm with diameter 6.5 mm) and polyester membranes (pore size 0.4 µm) were procured from Costar (Bedford, Mass.). The buffer components and solvents were obtained from Fisher Scientific (St. Louis, Mo.). All the di-peptide esters of acyclovir were custom synthesized in our laboratory. The dipeptide esters used for this study were: Val-Val-ACV, Tyr-Gly-ACV, Gly-Val-ACV, Gly-Gly-ACV, Gly-Tyr-ACV, Val-Tyr-ACV, and Tyr-Val-ACV.

Cell Culture All cultures were maintained in humidified incubator at 37° C. with a 5% carbon dioxide in air atmosphere. Caco-2 cells were obtained at passage 25 from American Type Culture Collection (ATCC) and grown in plastic tissue culture flasks. Conventional culture medium containing DMEM, 10% FBS (heat-inactivated), 1% NEAA, 4 mM L-glutamine, 100 IU/ml penicillin, 100 µg/ml streptomycin, and 14 mM HEPES at pH 7.4 was used as per the protocol established in our laboratory for maintaining the cell line. When 80% confluent, these cells were removed by treating them with Trypsin/EDTA and plated at a density of 100,000 cells/cm$^2$ on collagen coated plastic dishes containing clear polyester membranes (0.636 cm$^2$, 3.0 µm mean pore size) or 12-well tissue culture treated plastic plates. Cells were then grown in medium containing 10% FBS (heat-inactivated). Caco-2 cells employed in our studies were grown for 21-23 days. [$^{14}$C] Mannitol transport was determined as a marker of cellular integrity, which was <0.3% per hour in representative cell monolayers.

Metabolism studies in Cell Suspensions: Confluent Caco-2 cells, grown in tissue culture flasks were isolated with the aid of mechanical scraper and washed thrice with DPBS. The cells were resuspended in Dulbecco's Phosphate Buffer Saline-DPBS (pH-7.4) at a concentration of 1.0×10$^6$ cells/ml and 800 µl of the cell suspension was incubated with 200 µl of 1 mM solutions of ACV derivatives at 37° C. in a shaking water bath for the length of the study. One-hundred microliters of samples were withdrawn at predetermined time intervals and the sample was purified by precipitating the cellular proteins into the organic solvent mixture and stored at −80° C. until further analysis. The protein content of the cell suspension was determined by the method of Bradford using bovine serum albumin as the standard (BioRad protein estimation kit, Hercules, Calif.). Apparent first order rate constants were calculated and corrected for any chemical hydrolysis observed with the control.

Transport studies: Transport experiments were done using Side-bi-side™ diffusion cells (type VSC-1, Crown Glass Company Inc.) and Transwell® inserts. Prior to the experiment with Gly-Sar, Caco-2 cell monolayers grown on the clear polyester membranes and Transwell® inserts were washed with DPBS (pH 6.0) and incubated at 37° C. Freshly prepared drug solutions in DPBS (pH 6.0) was placed in the donor chamber and the receiver chamber was filled with DPBS. The volumes of donor and receptor chambers were 3 ml each for Side-bi-side™ diffusion cells and 0.5 ml and 1.5 ml respectively for Transwell® inserts. Sampling from the receiver chamber was done up to a period of 3 hours at time intervals of 15, 30, 45, 60, 90, 120, 150 and 180 minutes and fresh DPBS solution was replaced to maintain sink conditions in receiver chamber. The samples were stored at −80° C. until analyzed HPLC. All experiments were performed at 37° C. Transport studies with the ACV derivatives were also carried out using Side-bi-side™ diffusion cells. The pH dependent transport of Val-ACV and Gly-Val-ACV was assessed at pH's 6.0 and 7.4 at a concentration of 1 mM. Transport inhibition experiments of ACV esters with Gly-Sar were carried out at pH 6.0 as it has been reported as the pH of maximal transport for the prototypical oligopeptide transporter substrate, Gly-Sar (Guo et al., 1999). Concentration dependent transport of Gly-Val-ACV was also determined at varying concentrations (0.1-10 mM) and Michaelis-Menten parameters $K_m$ and $J_{max}$ were calculated.

Uptake studies: In typical uptake experiments, cell monolayers were incubated with the ACV derivative solutions prepared in DPBS (pH 6.0) for 10 minutes, except for time course studies. The concentration dependent uptake of glycylsarcosine was studied using [$^3$H] Gly-Sar along with varied concentrations (0.25-20 mM) of unlabeled Gly-Sar (pH 6.0). For affinity studies ACV esters (10 mM) were incubated along with radio labeled and unlabeled Gly-Sar for 10 minutes. For Dixon plots and Dose Response studies [$^3$H] Gly-Sar was incubated along with increasing concentrations (0.25-20 mM) of unlabeled Gly-Sar and Val-Val-ACV. Following incubation, the cell monolayers were washed three times with ice-cold HEPES buffer to terminate the uptake experiment. After the washings cells were lysed overnight using 1 ml 0.1% (w/v) Triton X-100 in 0.3 N NaOH at room temperature. Aliquots (500 µl) from each well were then transferred to scintillation vials containing 5 ml scintillation cocktail (Fisher Scientific, Fairlawn, N.J.). Samples were then analyzed by the liquid scintillation spectrophotometry using scintillation counter (Beckman Instruments Inc., Model LS-6500) and the rate of uptake was normalized to the protein content of each well. The amount of protein in the cell lysate was measured by the BioRad protein estimation kit using bovine serum albumin as standard (BioRad Protein estimation Kit, Hercules, Calif.).

Analytical Procedures: All samples were assayed using HPLC. The system comprised of a Rainin Dynamax Pump SD-200, Rainin Dynamax UV Detector UV-C at 254 nm, a HP 1100 series Fluorescence Detector at ex λ=285 nm, em λ=370 nm and an Alcott autosampler Model 718 AL HPLC. The column used was a C18 Luna column 4.6×250 mm (Phenomenex). The mobile phase consisted of a mixture of buffer and an organic modifier. The percentage of organic phase was varied in order to elute compounds of interest. This method gave rapid and reproducible results. HPLC conditions for the various compounds have been summarized in Table 1.

Data Analysis

Permeability Measurements across Caco-2 monolayers: Steady State Fluxes (SSF) were determined from the slope of the cumulative amount of drug transported versus time graph and expressed per unit of cross sectional surface area of the membrane as described by Eq. 1. The cumulative amount of drug transported is the sum of the receptor cell ACV derivative and the regenerated ACV.

$$\text{Flux } (J) = (dM/dt)/A \qquad \text{Eq. 1}$$

M is the cumulative amount of drug transported and A is the cross sectional surface area exposed to permeant. Caco-2 membrane permeabilities are determined by normalizing the SSF to the donor concentration, $C_d$ according to Eq. 2.

$$\text{Permeability } (P_{app}) = \text{Flux}/C_d \qquad \text{Eq. 2}$$

Affinity Calculations: The concentration dependent uptake of [$^3$H] glycylsarcosine was fitted to the modified Michaelis-Menten equation described in Eq. 3:

$$V = \frac{V_{max} * C}{K_m + C} + K_d * C \qquad \text{Eq. 3}$$

Eq. 3 takes into account both the carrier mediated process (as described by the classical Michaelis-Menten equation) and the non-saturable passive diffusion process. V represents the total rate of uptake. $V_{max}$ is the maximum rate of uptake for the carrier mediated process, $K_m$ is the permeant concentration where half the maximal rate is reached and $K_d$ is the rate constant for the non-saturable diffusion component. Concentration dependent transport of GVCAV was fitted to the classical Michaelis-Menten equation, which takes into account only the saturable component. $K_m$, $V_{max}$ and $K_d$ of uptake of [$^3$H] glycylsarcosine and transport of Gly-Val-ACV were determined using a non-linear least square regression analysis program (KALEIDAGRAPH V3.09). The quality of the fit was determined by evaluating the coefficient of determination ($r^2$), the standard error of parameter estimates and by visual inspection of the residuals.

All the compounds of the invention inhibited the uptake of [$^3$H] glycylsarcosine in a competitive manner, and the kinetics can be expressed according to Eq. 4

$$V = \frac{V_{max} * C}{K_m(1 + I/K_i) + C} \qquad \text{Eq. 4}$$

In Eq. 4 I is the concentration of the ACV derivative and $K_i$ is the inhibitor concentration. Affinities ($K_i$) for the various compounds were calculated by fitting the data to Eq. 4. The $K_i$'s for the drugs were also calculated by transforming the Michaelis-Menten equation 4 to Lineweaver-Burk equation, which yields the linear Eq. 5 for competitive inhibition, $$\frac{1}{V} = \frac{K_m * \left(1 + \frac{I}{K_i}\right)}{V_{max}} * \frac{1}{C} + \frac{1}{V_{max}} \qquad \text{Eq. 5}$$

From a plot of 1/V vs. 1/C, $V_{max}$ and $K_m$ and hence $K_i$ can be estimated by linear regression analysis.

The affinity of Val-Val-ACV was also calculated from Dixon transformation of Eq. 4 which yields Eq. 6:

$$\frac{1}{V} = \frac{K_m * I}{V_{max} * K_i * C} + \frac{1}{V_{max}}\left(1 + \frac{K_m}{C}\right) \qquad \text{Eq. 6}$$

For Dose response studies in which Gly-Sar uptake was inhibited, the inhibitory effect of unlabeled Gly-Sar and Val-Val-ACV was described by the model illustrated by Eq. 7:

$$E = \frac{E_0 * IC50^n}{IC50^n + I^n} \quad \text{Eq. 7}$$

The IC50 estimated from the Eq. 7 was used to calculate the $K_i$ of Gly-Sar and Val-Val-ACV by the method of Cheng and Prusoff (Cheng and Prusoff, 1973) in which $K_i$ is equivalent to $IC50/(1+C/K_m)$. The affinity of cephalexin, which was used as a positive control, was also evaluated in order to compare the $K_i$'s of the dipeptide ACV derivatives.

Statistical Analysis: All experiments were conducted at least in triplicate and the results are expressed as mean±SD except in the case of Michaelis-Menten parameters $K_m$, $V_{max}$, $K_d$ and the affinities, $K_i$ where the values are presented as mean±S.E. Student's t-test was used to detect statistical significance between the affinities of the dipeptide ACV derivatives and Val-ACV and p<0.05 was considered to be statistically significant. Statistical Significance was also tested by t-test between the affinities of the dipeptide ACV esters and cephalexin. Statistical comparisons between the affinities of various compounds were performed using the analysis of variance (SPSS for Windows Release 10.0.7. Chicago, Ill.).

Results

Figure 4:
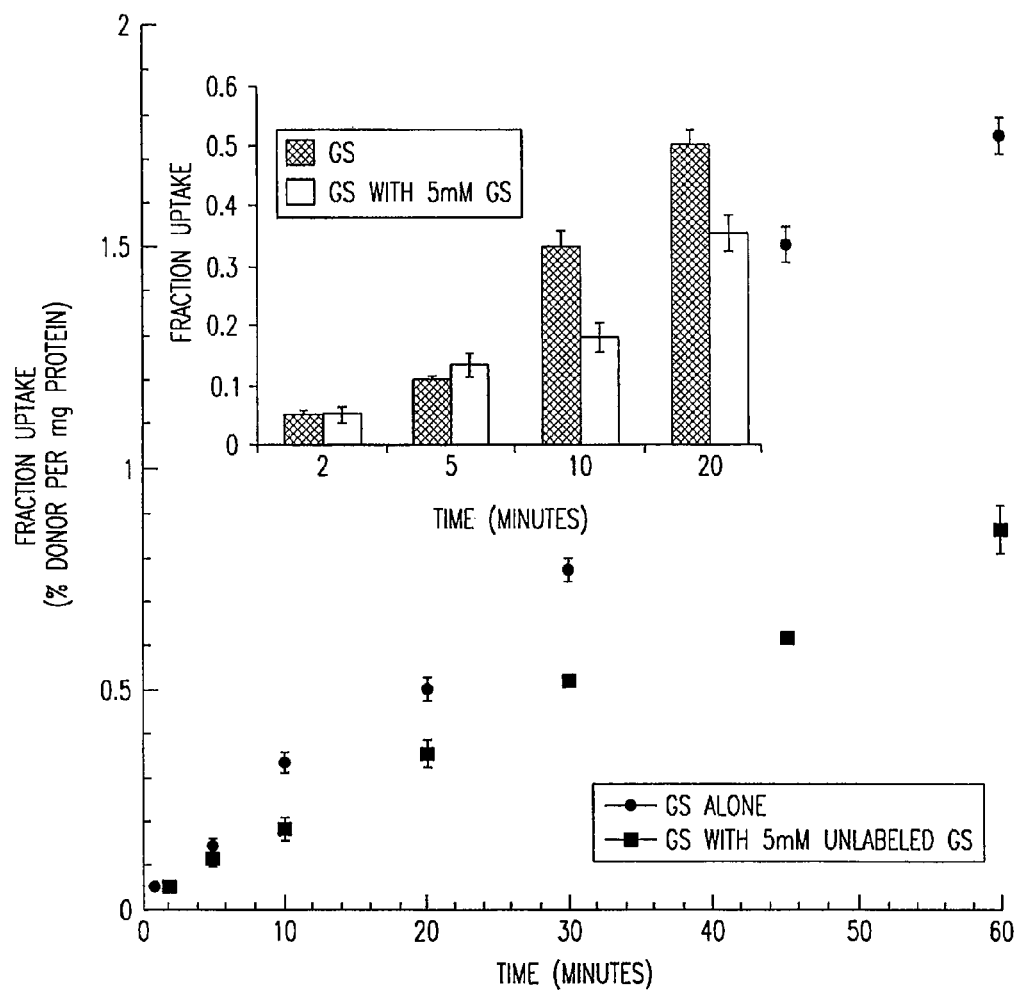
FIG. 4 shows the time dependence cellular uptake of [$^3$H] Glycylsarcosine: (●) [$^3$H] Gly-Sar alone; (■) [$^3$H] Gly-Sar with 5 mM unlabeled Gly-Sar. Inset, comparison of uptake of [$^3$H] Gly-Sar in presence of 5 mM Gly-Sar at various time intervals.
Figure 5:
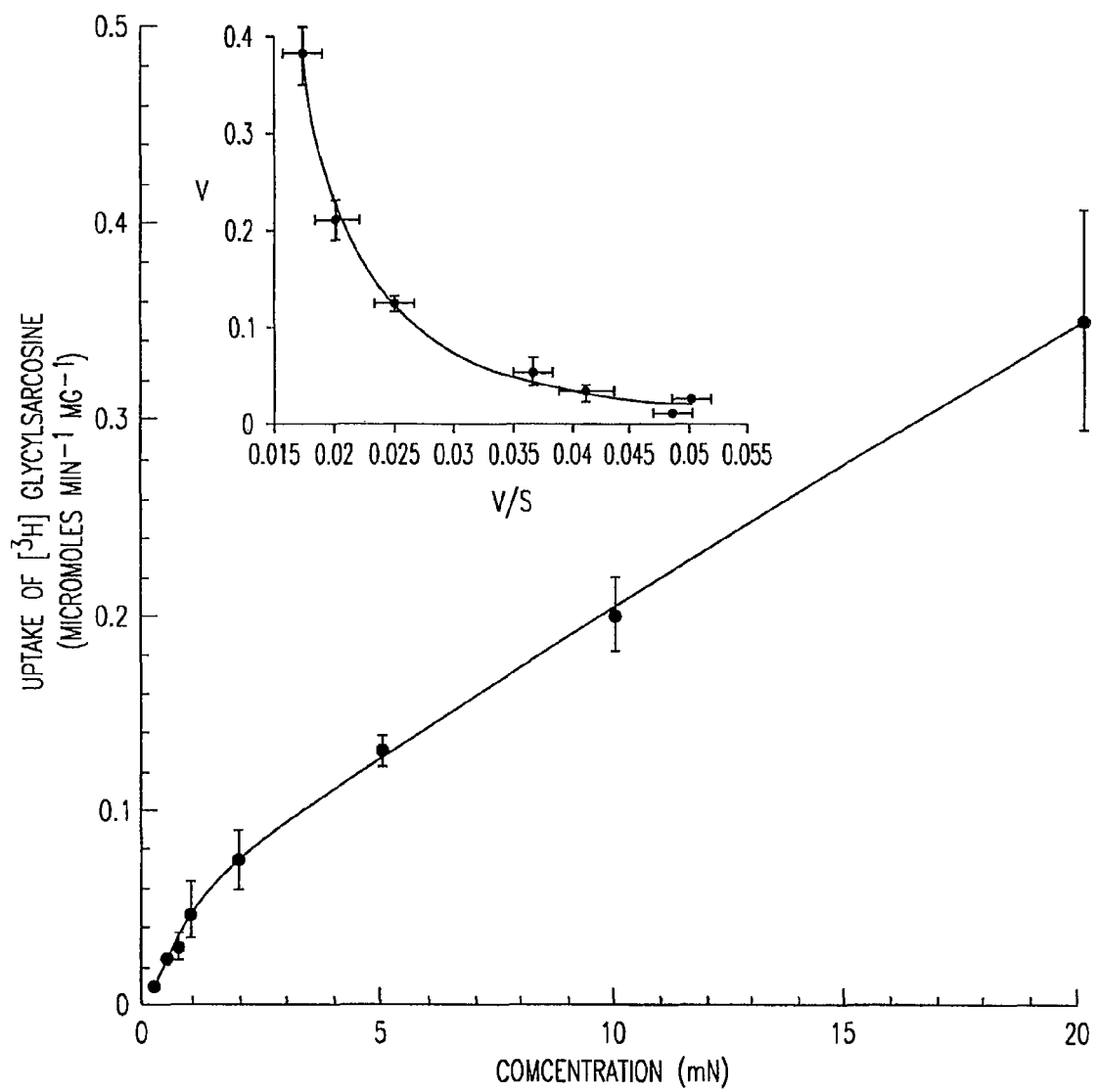
FIG. 5. is a graph of the concentration dependence cellular uptake of [$^3$H] Gly-Sar to Caco-2 cells. Inset, Woolf-Augustinsson-Hofstee transformation of the data V (micromoles $min^{-1}$ $mg^{-1}$) vs. uptake of [$^3$H] Glycylsarcosine/concentration, V/S (µl $min^{-1}$ $mg^{-1}$)]. Values are mean±S.D. (n=4).

Time and concentration dependent uptake of [$^3$H] Glycylsarcosine: The time course of Gly-Sar uptake (FIG. 4) was linear up to twenty minutes. As seen in the FIG. 4 inset the inhibition of [$^3$H] Gly-Sar uptake was significant after 10 minutes. Based on these results 10 minute uptake was performed for all the experiments to maximize the radioactivity uptake and also to allow for a significant inhibition within the linear region of the uptake. FIG. 5 demonstrates the uptake of glycylsarcosine as a function of concentration ($K_m$ 1.63±0.25 mM, $V_{max}$ 0.078±0.005 μmoles min$^{-1}$ mg$^{-1}$). The Caco-2 cell uptake of glycylsarcosine was found to comprise a nonsaturable component ($K_d$ 12.2±0.57 μl min$^{-1}$ mg$^{-1}$), which was deducted from the total uptake to calculate the saturable uptake. The Woolf-Augustinsson-Hofstee transformation of the data from the concentration dependent uptake of [$^3$H] Gly-Sar resulted in a biphasic transport process (inset, FIG. 5) for the mixed uptake (transport mediated and the passive diffusion component). However a linear Woolf-Augustinsson-Hofstee plot ($R^2$=0.89) resulted when only the saturable uptake component was plotted (data not shown). Therefore the kinetics of Gly-Sar uptake matched a single, saturable carrier model along with the linear diffusion component.

Caco-2 Metabolism Studies: The ACV derivatives hydrolyzed to yield the parent drug ACV in Caco-2 homogenates (Table 7). The percentage remaining of the intact ACV derivates after a 10 minute period ranged from 38-97%. The ACV derivatives hydrolyzed to the active parent drug, ACV. The dipeptide ACV derivative Gly-Gly-ACV was rapidly hydrolyzed (no intact drug detected within one minute) following incubation with the cell suspension and was therefore not used for further inhibition experiments.

TABLE 7

Enzymatic stability of dipeptide esters of Acyclovir

| Drug | $10^2 \times k_{obs}{}^a$ (min$^{-1}$ mg$^{-1}$ protein) | $t_{1/2}$ (min.) |
| --- | --- | --- |
| Val-ACV | 0.56 ± 0.038 | 123.7 ± 8.3 |
| Tyr-Val-ACV | 10.1 ± 0.46 | 6.9 ± 0.3 |
| Tyr-Gly-ACV | 5.22 ± 0.58 | 13.3 ± 1.5 |
| Gly-Tyr-ACV | 3.21 ± 0.46 | 21.5 ± 3.2 |

TABLE 7-continued

Enzymatic stability of dipeptide esters of Acyclovir

| Drug | $10^2 \times k_{obs}{}^a$ (min$^{-1}$ mg$^{-1}$ protein) | $t_{1/2}$ (min.) |
| --- | --- | --- |
| Val-Val-ACV | 2.14 ± 0.44 | 33.2 ± 6.9 |
| Gly-Val-ACV | 0.637 ± 0.01 | 108.1 ± 2.4 |
| Val-Tyr-ACV | 0.275 ± 0.03 | 250.4 ± 27.8 |
| Gly-Gly-ACV | * | — |

Figure 6:
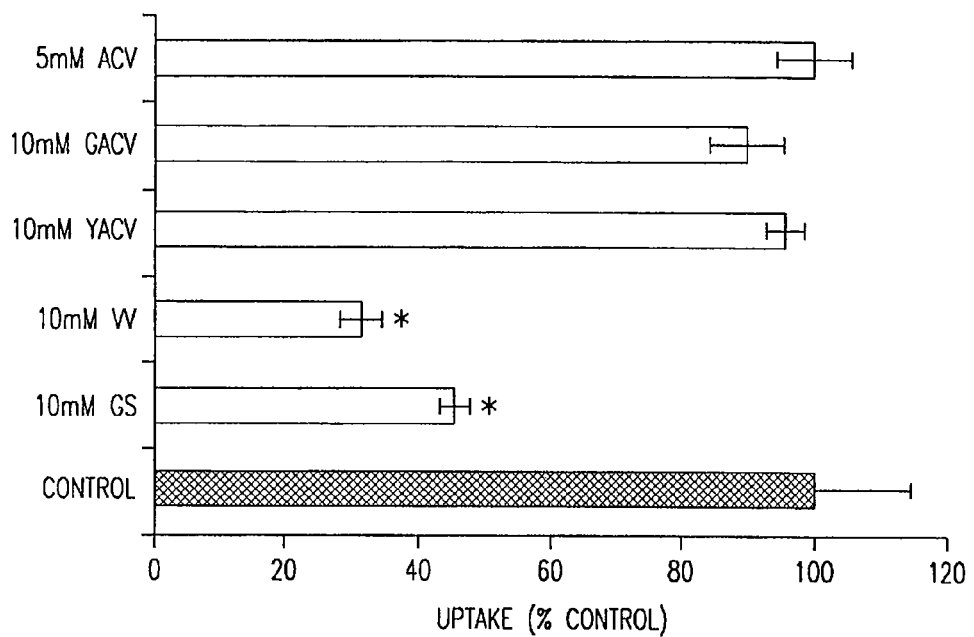
FIG. 6 shows the effect of tested compounds on the uptake of [$^3$H] Gly-Sar. Values are mean±S.D. (n=4).

Values are mean ± S.D. (n = 3-6)
$^a$measured using Caco-2 cell suspension at pH 7.4
* No intact drug detected during the experiment Uptake Experiments: All the ACV derivatives at a concentration of 10 mM were found to significantly inhibit the uptake of Gly-Sar. The amino acid derivatives, tyrosine-ACV, glycine-ACV and the parent drug acyclovir alone did not inhibit the uptake of [$^3$H] Gly-Sar whereas unlabeled glycylsarcosine and the dipeptide val-val significantly inhibited (p<0.05) the uptake of [$^3$H] Gly-Sar (FIG. 6). Lineweaver-Burk transformations of the Michaelis-Menten data showed that the ACV derivatives inhibited the uptake of glycylsarcosine in a competitive manner.

Lineweaver-Burk transformations of the uptake of Gly-Sar in presence of various ACV derivatives were of a competitive type revealing that the ACV derivatives shared a common enzyme site as that of Gly-Sar. Therefore it can be speculated that these ACV derivatives would be transported by the peptide transporter. The $V_{max}$ values of Gly-Sar in presence of all the ACV derivatives did not change as compared with control whereas the Km values were different (Table 8) confirming that the dipeptide ACV derivatives inhibited the uptake of Gly-Sar in a competitive manner.

TABLE 8

Comparisons of Kinetic Parameters for Glycylsarcosine. Effect of Dipeptide ACV derivatives on the inhibition of uptake of Glycylsarcosine.

| | $V_{max}$ (μmoles/min/mg) | $K_m$ (mM) |
| --- | --- | --- |
| Glcylsarcosine Parameters Gly-Sar | | |
| Michaelis-Menten | 0.078 ± 0.005 | 1.63 ± 0.25 |
| Lineweaver-Burk | 0.086 ± 0.019 | 2.04 ± 0.61$^a$ |
| Eadie-Hofstee | 0.071 ± 0.009 | 1.42 ± 0.19 |
| Gly-Sar (with drugs) Parameters Lineweaver-Burk | | |
| +Val-ACV | 0.081 ± 0.09 | 14.7 ± 1.32* |
| +Gly-Val-ACV | 0.095 ± 0.07 | 13.2 ± 1.97* |
| +Val-Val-ACV | 0.099 ± 0.10 | 12.8 ± 0.36* |
| +Val-Tyr-ACV | 0.092 ± 0.02 | 8.27 ± 0.92* |
| +Gly-Tyr-ACV | 0.094 ± 0.11 | 7.21 ± 2.61* |
| +Tyr-Val-ACV | 0.091 ± 0.07 | 7.01 ± 0.91* |
| +Tyr-Gly-ACV | 0.087 ± 0.09 | 4.51 ± 0.12* |
| +Cephalexin | 0.101 ± 0.03 | 4.08 ± 0.36* |

Figure 7:
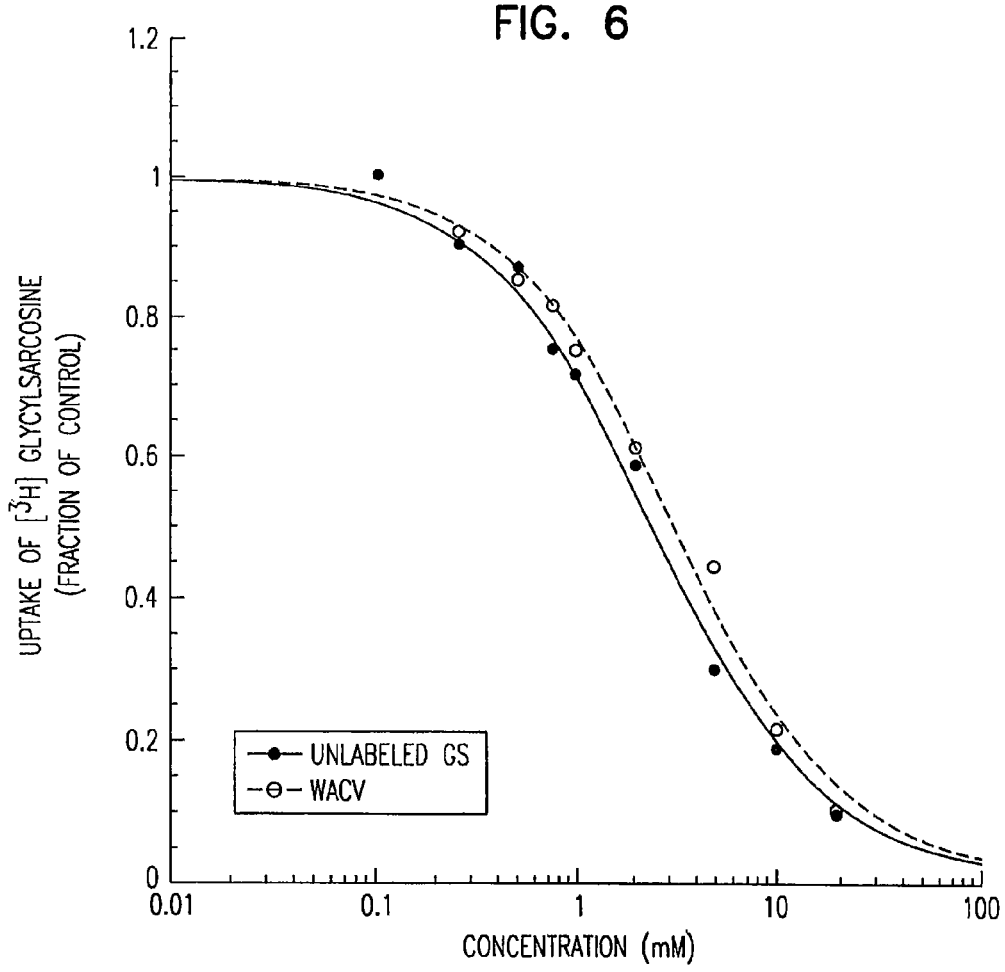
FIG. 7 is a dose response curve of the inhibition of cellular uptake of [$^3$H] Glycylsarcosine by (●) unlabeled glycylsarcosine; and (○) Val-Val-ACV.

Values are mean ± S.E. (n = 3-6)
$^a$Control
*p < 0.05 compared with control $K_i$ values of the ACV derivatives except Tyr-Gly-ACV (Table 4) were higher than that of cephalexin (p<0.05). The IC50 values of Gly-Sar and Val-Val-ACV from dose response curves (FIG. 7) were estimated by fitting the data to the nonlinear equation $E/E_0=1/(1+[I]/IC50)$ and were found to be 2.78±0.34 mM and 3.46±0.21 mM respectively. $K_i$ values were calculated by the method of Cheng and Prusoff (Cheng and Prusoff, 1973) and were estimated to be 2.49 mM and 3.18 mM for Gly-Sar and Val-Val-ACV respectively. $K_i$ values for Gly-Sar and Val-Val-ACV calculated by different approaches were in close agreement (Table 9).

TABLE 9

Affinities of various esters of Acyclovir and Cephalexin towards peptide transporter on the human intestinal Caco-2 cell line.

| | $K_i$ (mM) | |
|---|---|---|
| | Michaelis-Menten | Lineweaver-Burk |
| Val-ACV | 1.41 ± 0.56[a] | 1.61 ± 0.15 |
| Gly-Val-ACV | 1.42 ± 0.24[a] | 1.82 ± 0.34 |
| Val-Val-ACV | 1.94 ± 0.49[a] | 1.89 ± 0.22 |
| Val-Tyr-ACV | 2.97 ± 0.34[a,b] | 3.27 ± 0.71 |
| Gly-Tyr-ACV | 3.56 ± 1.98[a,b] | 3.94 ± 0.61 |
| Tyr-Val-ACV | 4.96 ± 0.97[a,b] | 4.11 ± 0.32 |
| Tyr-Gly-ACV | 7.99 ± 0.54[b] | 8.23 ± 0.43 |
| Cephalexin | 8.19 ± 2.12[b] | 9.97 ± 0.92 |
| Val-Val-ACV | Michaelis-Menten | 1.94 ± 0.49 |
| | Lineweaver-Burk | 1.89 ± 0.22 |
| | Dixon | 2.51 ± 0.29 |
| | Dose Response | 3.18 ± 0.18 |
| Glycylsarcosine | Dixon | 2.35 ± 0.67 |
| | Dose Response | 2.49 ± 0.13 |

Figure 8:
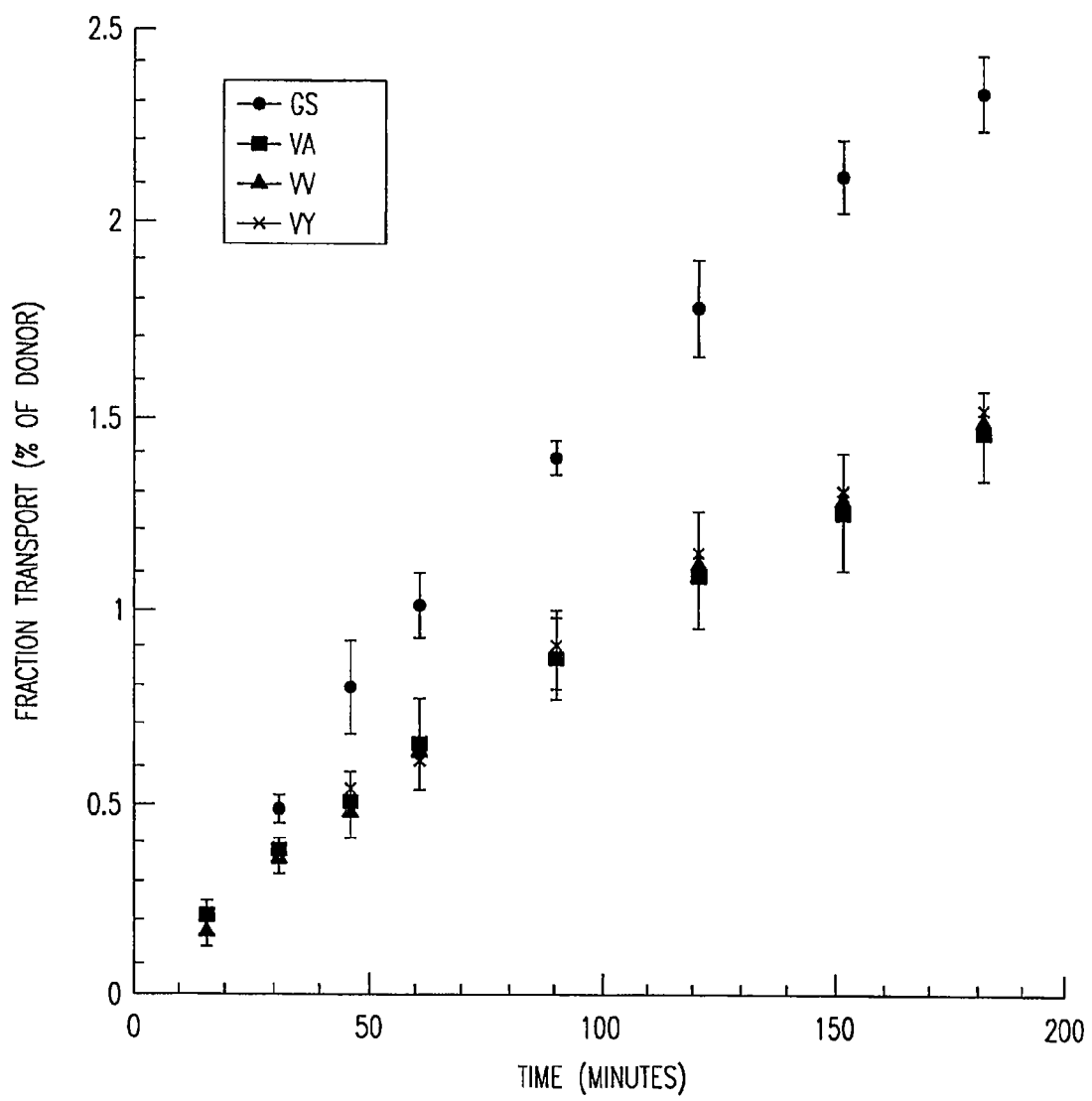
FIG. 8 is a graph of the transepithelial transport of [$^3$H] Glycylsarcosine in the absence (●) [$^3$H] Gly-Sar alone and presence of 10 mM concentrations of derivatives of Acyclovir: (■) [3H] Gly-Sar with Val-ACV; (▲) [$^3$H] Gly-Sar with Val-Val-ACV (X) [$^3$H] Gly-Sar with Val-Tyr-ACV.
Figure 9A:
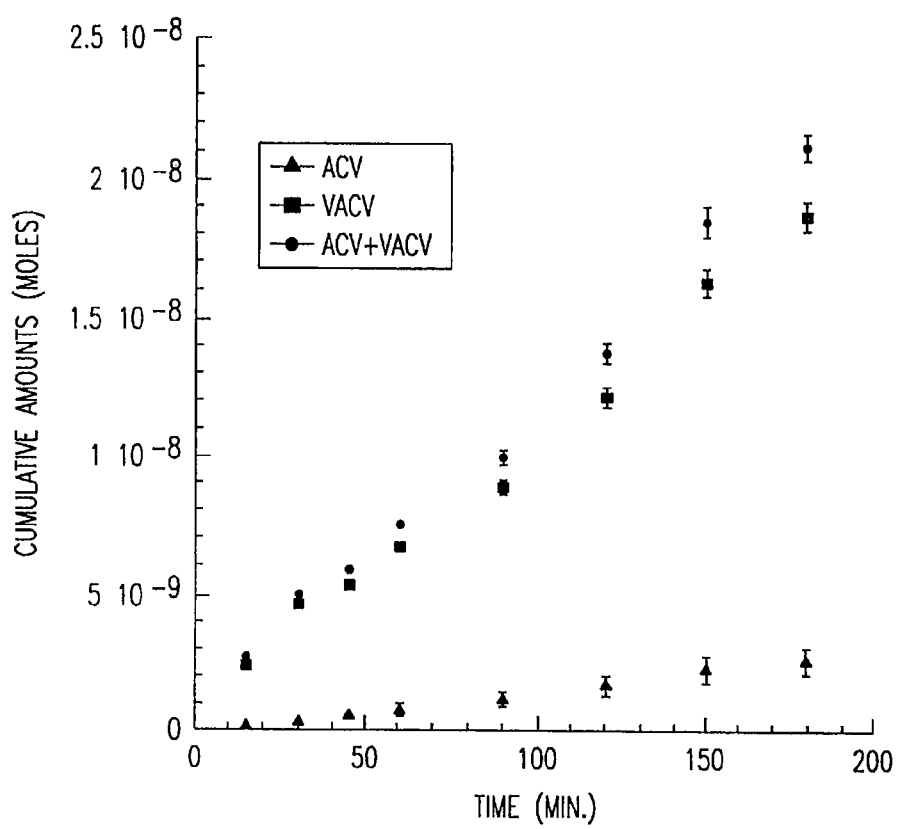
FIG. 9. Panel A is a permeation profile of L-Val-ACV into Caco-2 cells as a function of time: (▲) regenerated parent drug ACV; (■) intact L-Val-ACV; and (●) cumulative amount of L-Val-ACV ($R^2$=0.99). Panel B is a permeation profile of Gly-Val-ACV across Caco-2 as a function of time: (▲) regenerated parent drug-ACV; (■) Val-ACV; (♦) intact Gly-Val-ACV; and (●) cumulative amount of Gly-Val-ACV ($R^2$=0.98). (Mean±S.D., n=3).
Figure 9B:
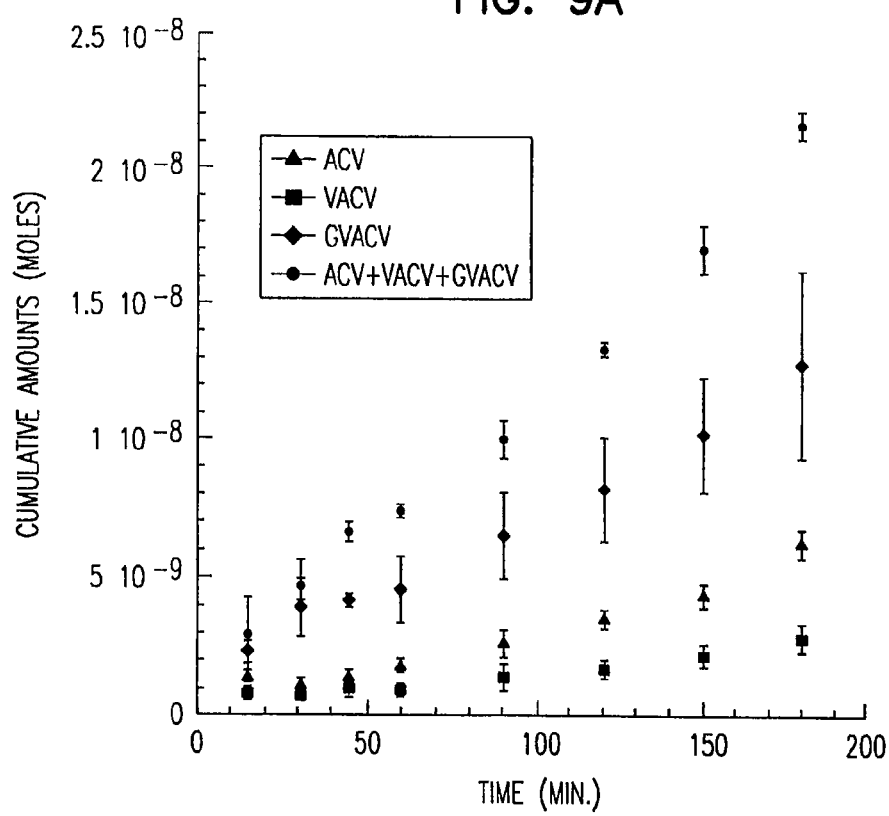
Figure 10:
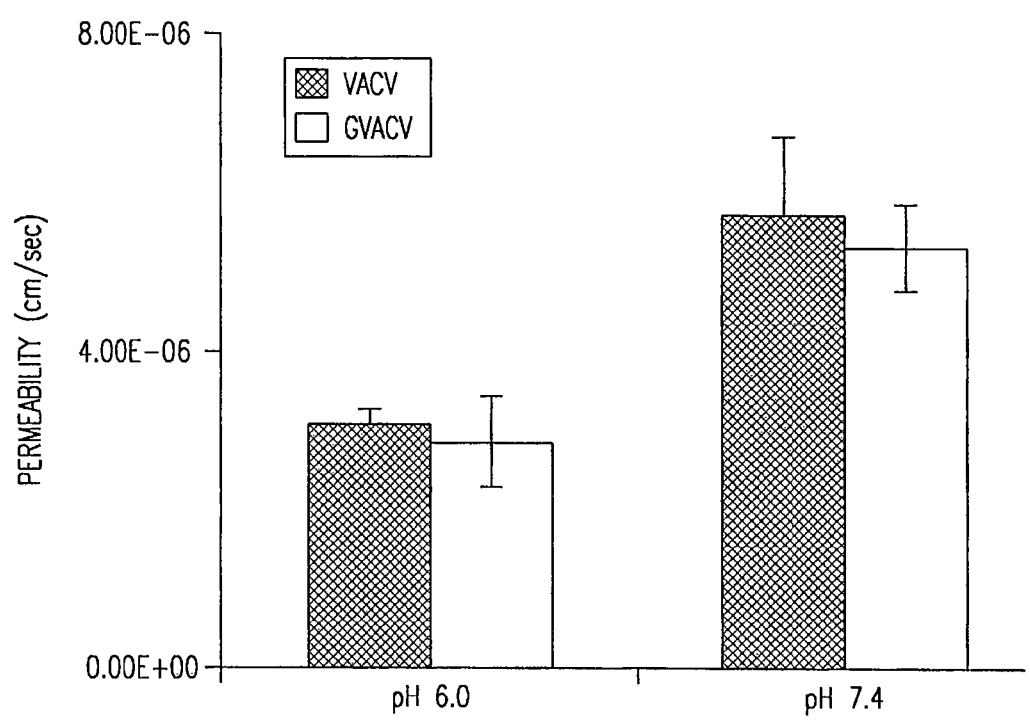
FIG. 10 is a graph of the permeability of a 1 mM concentration of Val-ACV and Gly-Val-ACV as a function of pH. * denotes p<0.05 compared to Val-ACV and Gly-Val-ACV permeabilities at pH 6.0. Values are mean±S.D. (n=3).
Figure 11:
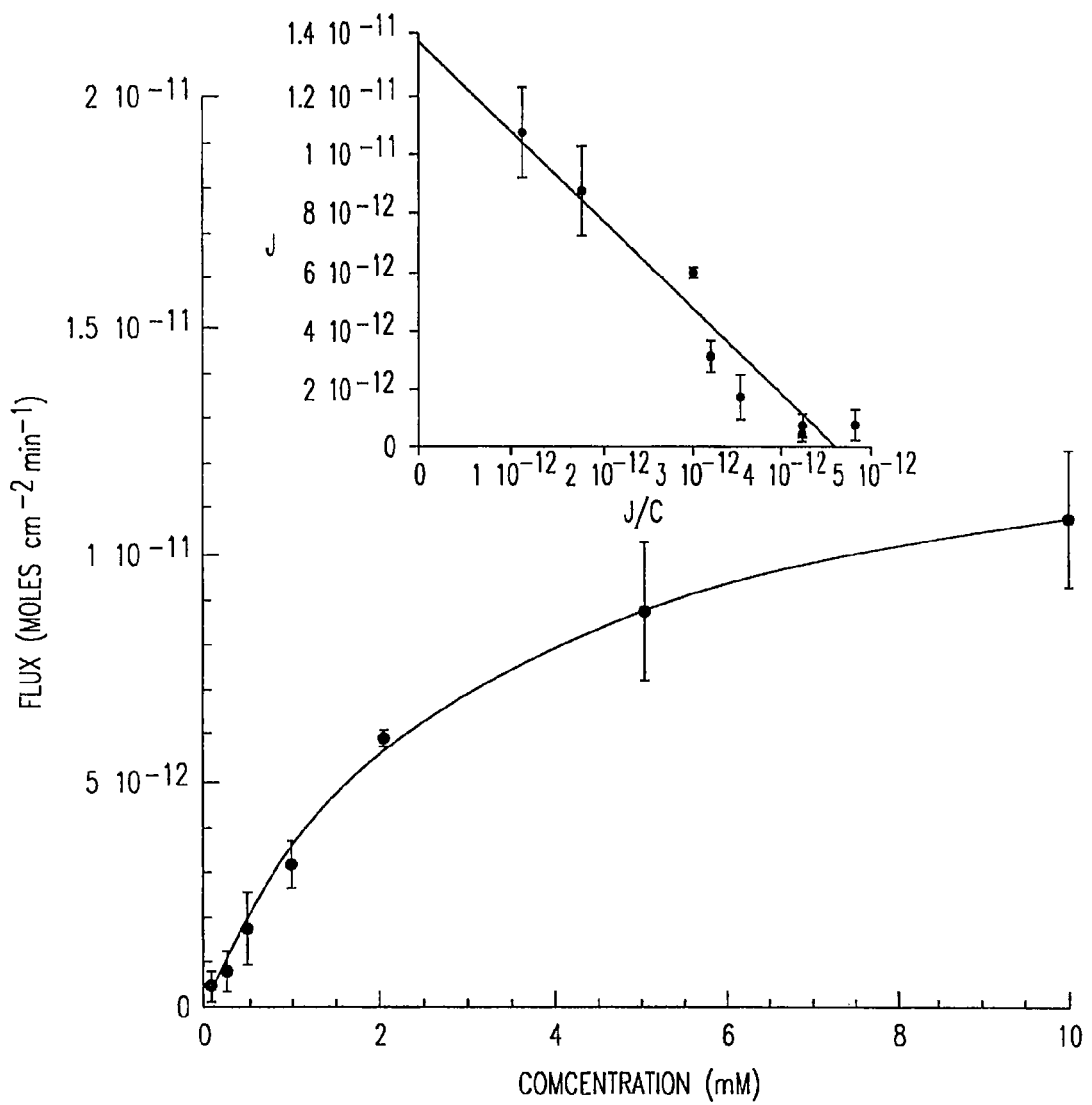
FIG. 11 shows the concentration dependence of transport of Gly-Val-ACV into Caco-2 cells ($R^2$=0.996). Inset, Woolf-Augustinsson-Hofstee linear transformation ($R^2$=0.935) of the data [Fluxes of Gly-Val-ACV, J (moles cm$^{-2}$ min$^{-1}$) vs. Fluxes of Gly-Val-ACV/concentration of Gly-Val-ACV, J/S]. Values are mean±S.D. (n=4-6).

Values are mean ± S.E. (n = 3-6)
[a]p < 0.05 compared with CEX
[b]p < 0.05 compared with Val-ACV Transport Experiments: The transport of [$^3$H] Gly-Sar in presence of 10 mM concentrations of Val-ACV, Val-Val-ACV and Val-Try-ACV was also studied using Transwell® inserts. The dipeptide esters of ACV significantly inhibited (p<0.05) the transepithelial transport of Gly-Sar (FIG. 8). Val-ACV, Val-Val-ACV and Val-Try-ACV had a similar effect on the inhibition of the transport of Gly-Sar. The transepithelial transport of 1 mM concentrations of Val-ACV and Gly-Val-ACV was also studied across Caco-2 monolayers. The cumulative amount of drug transported (the sum of the ACV derivative and the regenerated ACV) was plotted as a function of time (FIG. 9). Apparent permeabilities ($P_{app}$) were determined from the linear portion of the cumulative amount versus time plot. The results indicated that the permeabilities of Val-ACV (5.67±1.13×10$^{-6}$ cm/sec) and Gly-Val-ACV (5.23±0.57×10$^6$ cm/sec) at pH 7.4 across Caco-2 monolayers were comparable. Moreover the transport of Val-ACV and Gly-Val-ACV was found to be pH dependent with a $P_{app}$ of 3.01±0.21×10$^{-6}$ cm/sec at pH 6.0 as compared to 5.67±1.13× 10$^{-6}$ cm/sec at pH 7.4 for Val-ACV and a $P_{app}$ of 2.80±0.59× 10$^{-6}$ cm/sec at pH 6.0 as compared to 5.23±0.57×10$^{-6}$ cm/sec at pH 7.4 for Gly-Val-ACV (FIG. 10). Also the transport of Val-ACV and Gly-Val-ACV was significantly inhibited in the presence of 10 mM concentration of Gly-Sar (Table 4). The inhibition in transport of Val-ACV (47% inhibition) and Gly-Val-ACV (63% inhibition) in presence of Gly-Sar indicates the involvement of the oligopeptide transporter in the absorption of the amino acid and the dipeptide ester of Acyclovir. The concentration dependent transport of Gly-Val-ACV comprised of a saturable component with a $K_m$ of 3.16±0.31 mM and $V_{max}$ as 0.014±0.00058 moles cm$^2$ min$^{-1}$ (FIG. 11). Transformation of the data from the transport of Gly-Cys-ACV resulted in a Woolf-Augustinsson-Hofstee plot ($R^2$=0.935) (FIG. 11, inset). The kinetics of Gly-Val-ACV transport matched a single, saturable carrier model.

Conclusions

The studies in this Example show the dipeptide esters of ACV exhibit competitive inhibition of transport of Gly-Sar into Caco-2 cells. This suggests they share a common transporter, which is likely to be the PEPT1 transporter.

In addition to the inhibition data the concentration dependent transport of Gly-Val-ACV was found to be saturable at higher concentrations ($K_m$ 3.16±0.31 mM; $V_{max}$ 0.014±0.00058 moles cm$^{-2}$ min$^{-1}$) (FIG. 11). Transformation of the data resulted in a linear Woolf-Augustinsson-Hofstee plot ($R^2$=0.935) (FIG. 11, inset) and therefore the kinetics of Gly-Val-ACV transport matched a single, saturable carrier model. The $K_i$ and $K_m$ of Gly-Val-ACV were found to be very similar further confirming the sharing of the same binding site on the transporter.

The Caco-2 cell suspension hydrolysis studies were carried out in order to evaluate the regeneration characteristics of the ACV derivatives to ACV. All the ACV derivatives hydrolyzed to regenerate the active parent drug, ACV. The half-lives of the ACV derivatives ranged from 6.92 to 250.4 minutes (Table 2) demonstrating varied susceptibility of the ACV derivatives to the intestinal cellular enzymes.

Thus, the results of this Example indicate that the dipeptide esters of ACV, a poorly absorbed antiviral nucleoside, exhibit high affinity towards the intestinal oligopeptide transporter. The uptake of these esters was efficiently mediated by hPEPT1 as they significantly inhibit the uptake of glycylsarcosine. These esters hydrolyze readily to regenerate the active parent drug, acyclovir, thereby fulfilling the basic requirement of a prodrug. These compounds owing to their high affinity, excellent solution stability and in vitro antiviral activity against herpes infections are expected to be effective drugs against oral and ocular herpes infections.

Example 11

Ocular Penetration of Acyclovir and its Peptide Esters Valacyclovir and Val-Valacyclovir Following Systemic Administration in Rabbits In this Example, ACV and its valine (Val-ACV) and dipeptide (Val-Val-ACV) esters were administered systemically, and the levels of ACV and the ester in the blood, aqueous humor, and vitreous humor were measured to determine whether the ACV derivatives enhanced uptake into the eye, and whether the drugs reached the anterior segment (aqueous humor) or posterior segment (vitreous humor) or both. A dual probe technique to sample the anterior and posterior segments of the eye has been developed and is used in this Example. See Macha, S. et al., *Exp. Eye Res.* 72:289-299 (2001). In this model, integrity of the blood ocular barriers is maintained making it suitable to study the pharmacokinetics of a drug in both chambers of the eye. This model can be utilized to sample both the anterior and posterior segment of the same eye after drugs are administered either intravitreally or systemically.

Materials and Methods $^3$[H] glycylsarcosine (GS) was obtained from Morovek biochemicals while unlabelled GS was obtained from Sigma chemicals. Concentric CMA/20 microdialysis (polycarbonate membrane with 10 mm length) probes used for sampling of vitreous humor were obtained from CMA/Microdialysis (Acton, Mass.). Linear microdialysis probes (polyacrylonitrile membrane with 10 mm length) used for the sampling of aqueous humor were purchased from Bioanalytical systems (West Lafayette, Ind.). Microinjection pump (CMA/100) used for perfusing isotonic phosphate buffer saline (IPBS) through the probes, was obtained from CMA/Microdialysis. Ketamine HCl and Xylazine were purchased from Fort Dodge animal health and Bayer animal health respectively. Nembutal Sodium was obtained from Abbott laboratories (Abbott Park, Ill.). Tropicamide was supplied by Bausch & Lomb. New Zealand male albino rabbits weighing between 2-2.5 kg were purchased from Myrtle's Rabbitry (Thompson Station, Tenn.).

Animal Model:

New Zealand male albino rabbits weighing 2-2.5 kg were used as the animal model and were maintained under anesthesia throughout the experimental procedure. Ketamine hydrochloride (50 mg/kg) and xylazine (5 mg/kg) were injected intramuscularly as needed to maintain anesthesia throughout the experiment. The animals were euthanized by an overdose of sodium pentobarbital (50 mg/kg) to the marginal ear vein at the completion of an experiment. All experimental protocols followed the Association of Research in Vision and Opthalmology (ARVO) guidelines on the use of animals.

Microdialysis Probe Calibration:

In vitro probe calibration was conducted by placing the probe in the drug solution of known concentration. The probe was perfused at a flow rate of 2 µl/min with isotonic phosphate buffer saline (IPBS) and the dialysate was collected every 30 min. Relative recovery was calculated by the following formula, $$\text{Recovery factor} = C_d/C_s$$

$C_d$ is the dialysate concentration and $C_s$ is the known concentration of the drug in IPBS. The actual ACV or ester concentrations in the vitreous and aqueous humors were obtained by dividing the concentration in the dialysate samples by the in vitro recovery factor obtained.

Ocular Bioavailability Experiments:

Probe implantation: The anesthetized rabbit was placed on its left side. Then, 1-2 drops of tropicamide were applied to the right eye to dilate the pupil. A linear microdialysis probe was placed in the anterior chamber using a 25 G needle. The needle was inserted across the cornea carefully such that it stayed above the iris-ciliary body. The outlet of linear probe was placed into the needle at the bevel edge. The needle was then slowly withdrawn as the probe was pulled simultaneously into the anterior chamber. A concentric probe was placed in the vitreous body with the help of a 22 G needle, which was inserted into the vitreous at about 3 mm below the corneal scleral-limbus at a 45 degree angle. The probe was placed in the mid vitreous immediately after removing the needle under microscopic view. The microdialysis probes were perfused with isotonic phosphate buffer saline at a flow rate of 2 µl/min by a microinjection pump. Subsequent to probe implantation, the animals were allowed to stabilize for two hours prior to the initiation of an experiment.

Systemic administrations of ACV and its esters: A 27 G needle connected to a narrow diameter tubing was employed to infuse the drug into the marginal vein of the right ear. Dosing solutions containing esters equivalent to 30 mM (~7 mg) of ACV per ml were used. A constant volume (2.25 ml) of the dosing solutions were infused over 45 min by a microinjection pump at 50 µl/min. Samples were collected at appropriate time intervals beginning with the time the infusion was stopped (time zero) ending at 6 hours post infusion time.

$^3$[H] GS experiments: Experiments with GS were conducted to obtain a preliminary indication about the presence of a carrier mediated mechanism for small peptides. This was essential as no literature exists to indicate the presence of such a transport mechanism on the blood ocular barriers. The experimental setup was similar to the studies described previously. Rabbits were divided into two groups; a control group and a study group. The details of the protocol for this set of experiments are summarized in Table 10. Samples were collected for 10 hours after the dose was administered.

TABLE 10

| Protocol | Control | Experimental |
|---|---|---|
| Ketamine 50 mg/kg & Xylazine 5 mg/kg. | Anesthetized | Anesthetized |
| 90 mins after probe implantation | — | 1 ml (80 mg unlabelled GS) into the right marginal vein. |
| 120 mins after probe implantation (0 time for sampling) | 1 ml containing 10µCi $^3$[H] GS to the right marginal ear vein | 1 ml containing 10µCi $^3$[H] GS and 80 mg unlabelled GS to the right marginal ear vein |
| Aqueous and vitreous sample collection | Right eye | Right eye |
| Blood samples | Left ear vein | Left ear vein |

Blood sampling: The middle ear vein of the rabbit was used to obtain blood samples. A cannula consisting of a 22 G needle attached to a PE-50 tubing was implanted for withdrawing blood. The other end of the tubing was connected to a tuberculin syringe containing heparinized saline (100-units/ml). First 50 µl of withdrawn blood was discarded and subsequently 100 µl of blood was collected. After collection of blood ~150 µl of heparin was injected into the vein. Blood samples were then centrifuged at 5000 rpm for 15 min and the supernatant (plasma) was collected. An aliquot (40) µl of plasma was then diluted with 80 µl acetonitrile:methanol (5:4) mixture, vortexed thoroughly and centrifuged at 10,000 rpm for 15 min. Fifty µl supernatant was collected and assayed for the analyte with a LC-MS method described later. For experiments conducted with $^3$[H] GS, the plasma was directly used for radioactivity counting.

Sample analysis: The LC/MS system comprised of a Spectra System AS3000 auto sampler, P4000 solvent delivery system, UV6000 LP variable wavelength UV-VIS detector and Finnigan aQa single-quadruple mass spectrophotometer equipped with an electrospray source. The samples (20 µl) were injected into the electrospray at 300 µl min$^{-1}$ flow rate. Solvents used were water and acetonitrile with 0.1 TFA. A gradient method was utilized with acetonitrile proportion increasing linearly from 5% to 95% in 8 min. A C8 column (Alltech associates) 10 cm in length was employed for sample separation. The mass spectra were acquired with selected ion monitoring (SIM) at positive mode of the ESI probe (+30 V) with tune settings 0.8 (+V) for the radio frequency lens, 12.5 for both low and high mass resolutions and 650V for the detector. The ESI probe temperature was 350° C. and the probe voltage was set at 4.50 kV. A PC using Xcalibur software controlled all the devices. Radioactive samples were analyzed using a Scintillation counter (Beckman, LS 6500, multipurpose scintillation counter).

Results

Figure 12:
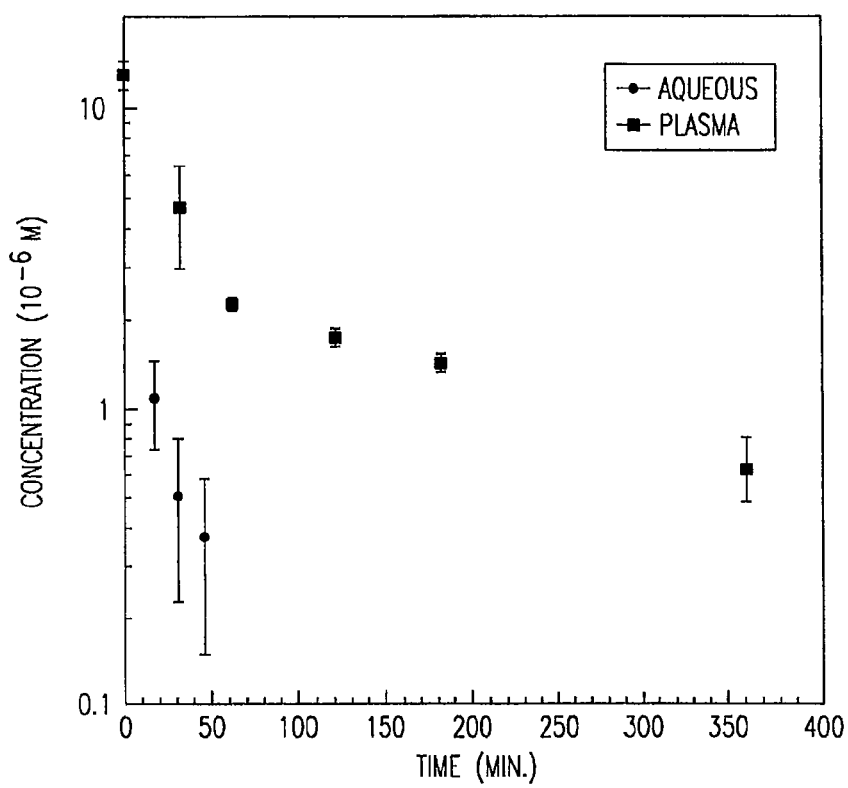
FIG. 12 is a graph of the concentration of Acyclovir (ACV) plasma and the anterior segment of the eye over time after intravenous infusion.
Figure 13:
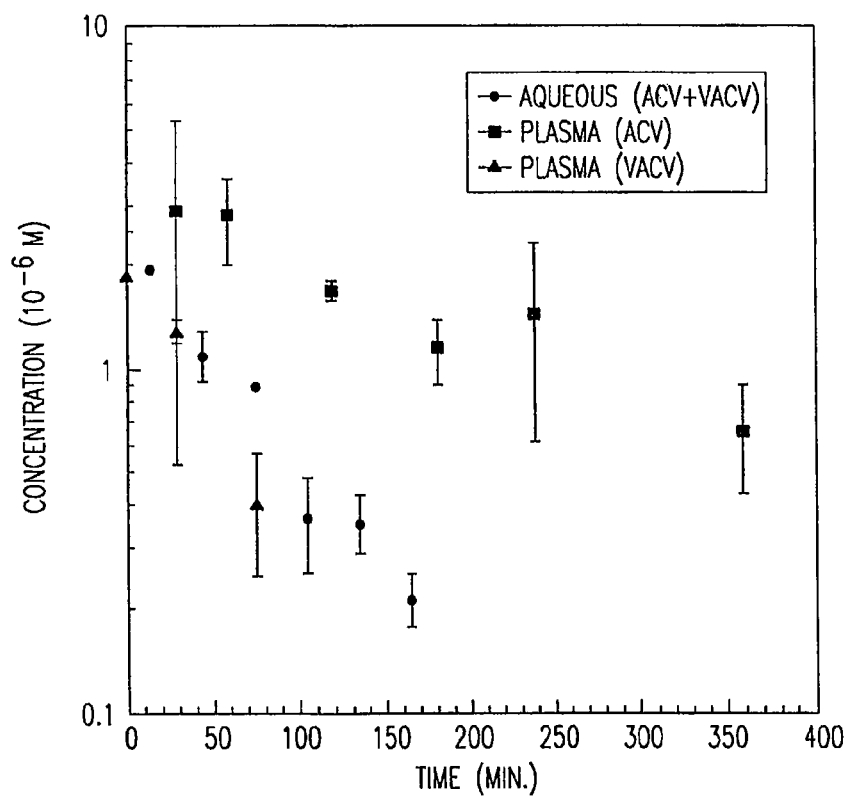
FIG. 13 is graph of the concentration of Valacyclovir (Val-ACV) in plasma and the anterior segment of the eye over time after intravenous infusion.
Figure 14:
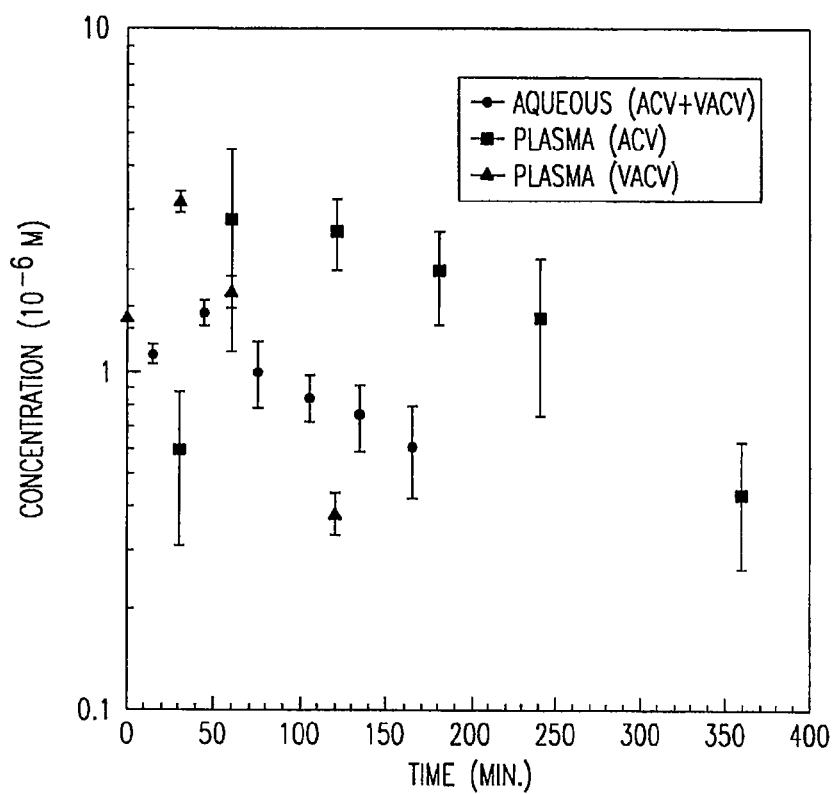
FIG. 14 is a graph of the concentration of Val-Valacyclovir (Val-Val-ACV) in plasma and the anterior segment of the eye over time after intravenous infusion.
Figure 15:
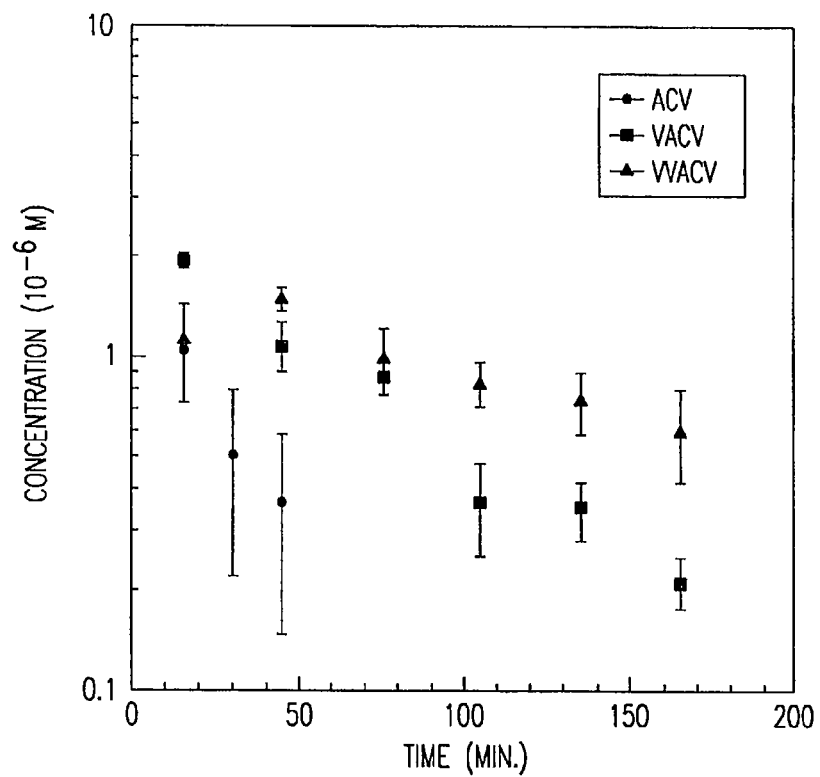
FIG. 15 is a comparison of the concentrations of ACV, Val-ACV and Val-Val-ACV in the anterior segment of the eye over time after intravenous infusion.

Ocular Bioavailability of ACV and its Esters:

ACV, Val-ACV and Val-Val-ACV were administered as intravenous infusions in New Zealand albino rabbits at the same molar equivalent doses. The plasma profile (post infusion) for ACV shows a bi-exponential curve with an initial distribution phase lasting for about 60 min followed by an elimination phase (FIG. 12). The aqueous humor samples showed presence of ACV for about one hour after infusion was stopped. No ACV was detectable in the vitreous humor. The aqueous and plasma pharmacokinetic profiles were subjected to a non-compartmental modeling approach. ACV exhibited a short plasma half-life of 167.61 (±36.94) min. FIGS. 13 and 14 represent the plasma profiles and the penetration of Val-ACV and Val-Val-ACV into the anterior segment of the eye respectively. Both Val-ACV and Val-Val-ACV are very rapidly hydrolyzed to ACV in the systemic circulation. In the case of Val-ACV, the ester readily converts to ACV whereas Val-Val-ACV hydrolyzes to generate Val-ACV and ACV. Val-Val-ACV was not detectable in the plasma at 30 min after infusion indicative of its very rapid hydrolysis to Val-ACV and ACV (FIG. 14). Aqueous humor samples indicated the presence of both the ester and the parent drug. In the case of Val-Val-ACV, there was no Val-Val-ACV detected in the aqueous humor and only Val-ACV and ACV were found to be present in these samples. Once again there was no detectable drug in the vitreous humor dialysate samples. The aqueous profiles in FIGS. 14 and 15 represent the sum total molar amounts of ester and ACV present in the aqueous humor, which represent the total drug levels in the aqueous humor. The comparative aqueous humor profiles (FIG. 15) indicate that both Val-ACV and Val-Val-ACV penetrated the BAB more efficiently as compared to ACV. The drug levels produced in the aqueous humor are much higher and more prolonged with ester administration as compared to ACV alone. Aqueous profiles were fitted by a Non Compartmental approach using WinNonlin™ and relevant pharmacokinetic parameters were compared (Table 11). With ACV derivatives the AUC's for the plasma and aqueous humor profiles were obtained by using the sum total of the molar concentrations of the ACV derivative and parent drug. Extent of drug penetration into the anterior segment of the eye was calculated by $AUC_{aqueous}/AUC_{plasma}$. Penetration ratios indicate that availability of ACV into the anterior segment of the eye was 4 and 8 fold better with Val-ACV and Val-Val-ACV administrations respectively. The mean residence times in the anterior segment of the eye increased with ACV derivative administration (Table 11). With ACV derivatives the area under the curves (AUCs) for the plasma and aqueous humor profiles were obtained by using the sum total of the molar concentrations of the ACV derivative and parent drug. Extent of drug penetration into the anterior segment of the eye was calculated by $AUC_{aqueous}/AUC_{plasma}$. Penetration ratios indicate that availability of ACV into the anterior segment of the eye was 4 and 8 fold better with Val-ACV and Val-Val-ACV administrations respectively. The mean residence times in the anterior segment of the eye increased with ACV derivative administration (Table 11). All of the data was statistically tested using SPSS.

TABLE 11

Ocular penetration and plasma bioavailability of the tested compounds.

| Compound | AUC aqueous$_{(t=0-c)}$ (min * μmoles/L) | MRT$_{(aqueous)}$ (min) | AUC plasma$_{(t=0-c)}$ (min * μmoles/L) | Penetration ratio |
|---|---|---|---|---|
| ACV | *53.70 (±35.58) | 46.47 (±24.94) | 896.24 (±143.58) | 0.05 (±0.03) |
| Val-ACV | *139.85 (±9.43) | 76.30 (±7.24) | 776.54 (±197.52) | 0.19 (±0.05) |
| Val-Val-ACV | *291.05 (±88.13) | *188.39 (±80.73) | 824.69 (±217.43) | *0.39 (±0.22) |

Values are Mean (±S.D.)
Penetration ratio = AUC aqueous/AUC plasma
*Values are significant at p < 0.05 level.

Figure 16:
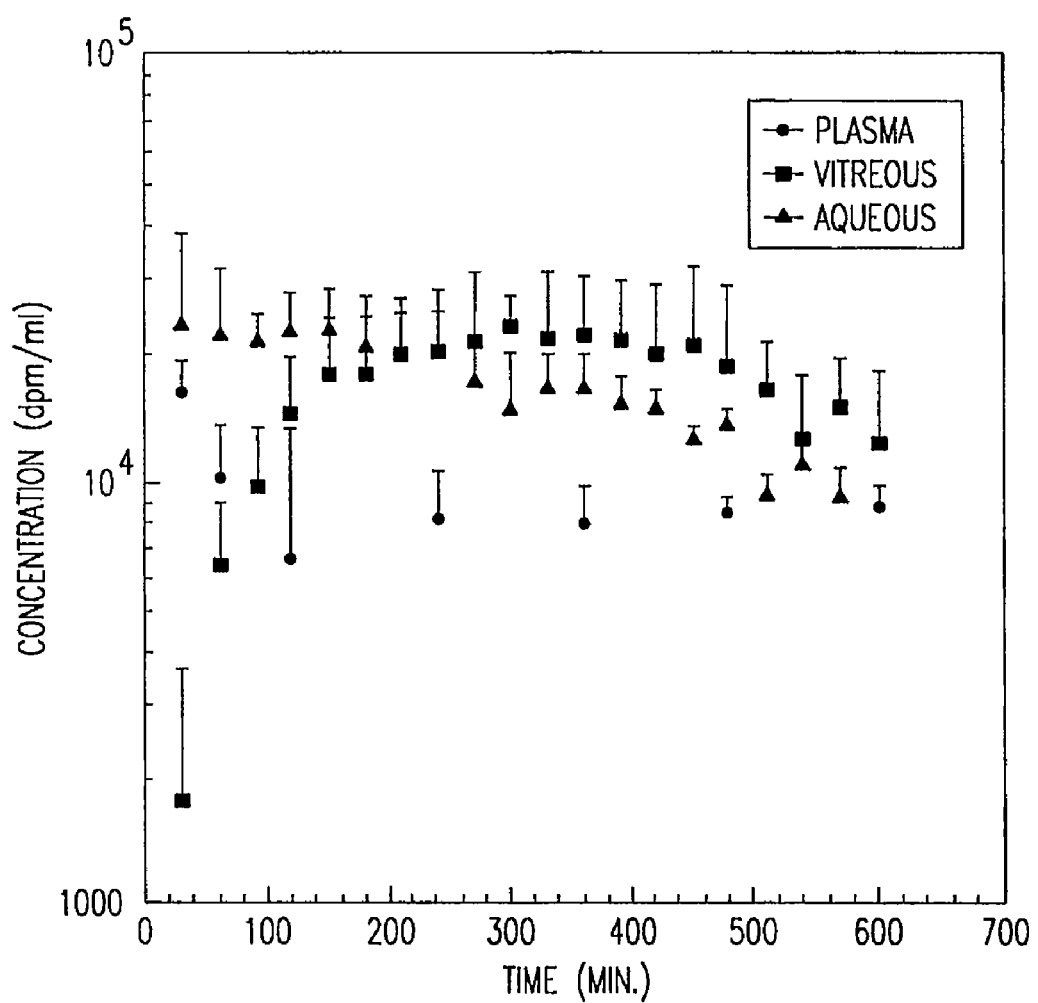
FIG. 16 shows the time profile of the concentration of $^3$[H] glycylsarcosine in the plasma, the anterior segment of the eye (aqueous) and the vitreous humor of the eye (vitreous) after systemic intravenous infusion.

Ocular Penetration of $^3$[H] Glycylsarcosine (GS):

Radiolabeled GS was administered systemically as an I.V. bolus dose (10 μCi). The dipeptide exhibited biexponential behavior with a rapid distribution and very slow elimination rate from the body (FIG. 16). Plasma levels were very low as compared to the administered dose indicative of a high volume of distribution attributable to the rapid uptake by the peptide transporters in various tissues. Both aqueous and vitreous compartments exhibited high levels of GS. Ratios of ocular levels to plasma were higher than unity at steady state indicating that a transporter-mediated ocular uptake process may be involved. Profiles were subjected to non-compartmental modeling. Area under curve (AUC) values of vitreous and aqueous were much higher as compared to the AUC of plasma. The penetration ratios further indicated the active secretion of GS into the eye (Table 12).

TABLE 12

Penetration of $^3$[H] glycylsarcosine in the presence and absence of inhibitor in rabbits.

| Rabbits | $AUC_{aq}/AUC_{blood}$ | $AUC_{vit}/AUC_{blood}$ |
|---|---|---|
| Control | 1.70 | 1.33 |
|  | 1.71 | 1.32 |
|  | 1.96 | 2.18 |
| Study (inhibitor) | 1.42 | 1.35 |
|  | 1.09 | 2.41 |
|  | 1.50 | 1.68 |
|  | 1.21 | 1.30 |

Aqueous penetration ratios of the control group were significantly different from the study group at p < 0.05. AUC is area under the curve.

Figure 17A:
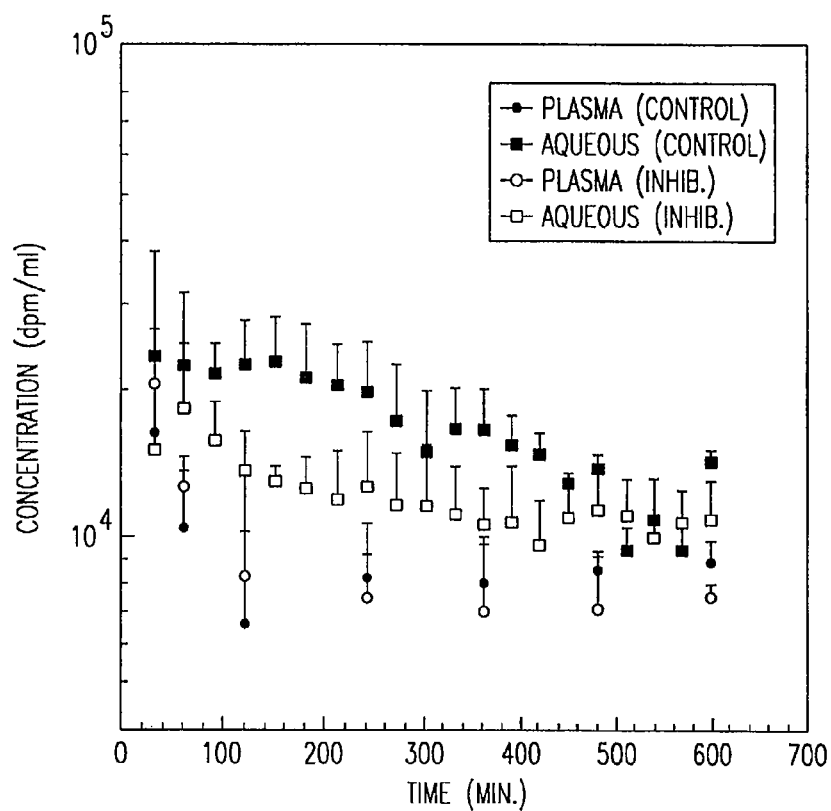
FIG. 17. Panel A shows the anterior segment penetration of $^3$[H] glycylsarcosine in the presence and absence of inhibitor. Panel B shows the posterior segment penetration of $^3$[H] glycylsarcosine in the presence and absence of inhibitor.
Figure 17B:
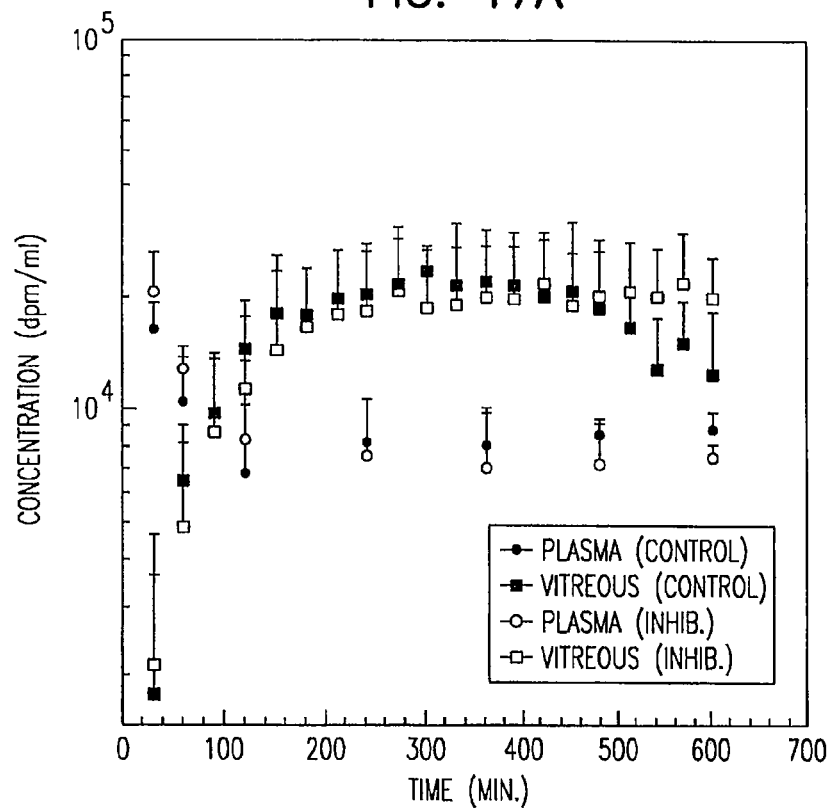

In the experimental group, an I.V. dose of 80 mg unlabelled GS was administered 30 min prior to the radioactive dose. In addition the radioactive dose was prepared in a solution of unlabelled GS (80 mg/ml). FIG. 17, panel A represents the comparative aqueous and plasma levels in the control and experimental groups. The plasma levels of $^3$[H] GS did not change due to the administration of unlabelled GS. However there was a decrease in the aqueous levels of radiolabeled drug indicating that the penetration of GS was inhibited to some extent. FIG. 17, panel B represents the comparative vitreous and plasma levels in the control and experimental groups. In this case there was no effect seen in the vitreous levels and the profiles almost overlapped.

The penetration ratios calculated in each case were subjected to a student t-test to determine any statistical significance. Penetration ratios indicate that the aqueous penetration of GS decreased in presence of the unlabelled GS. However, the penetration ratios in the vitreous humor exhibit high variability among the control and the experimental groups leading to inconclusive results.

Conclusion

The blood-ocular barriers, like the blood-brain barrier, restrict the movement of drugs. The BAB, however, has been shown to facilitate the movement of endogenous molecules such as ascorbate and lactate, indicating the presence of transporters for these compounds. Thus, the experiments of the present Example were undertaken to determine whether the compounds of the invention, by binding to transporters, were able to penetrate the blood-ocular barrier.

The valine ester and the Val-Val ester of ACV both penetrated the anterior segment of the eye to a higher extent than ACV itself. Experiments with GS revealed that the compound penetrated both segments of the eye probably via a carrier mediated transport pathway. Preliminary data presented here strongly indicates the presence of a functional transporter involved in the transport of small peptides. It also provides a plausible explanation for the enhanced permeation of the peptide ACV derivatives of ACV. The presence of a transporter on the blood ocular barriers can be exploited to deliver drugs to the inner ocular tissues via either the intravenous or the oral route. Such a strategy can have major implications in ocular drug delivery especially in instances where the patient suffers from an ocular infection as well as an extra-ocular disease.

Example 12

Novel Dipeptide Esters of Acyclovir for Ocular Herpes Infections: Bioreversion, Antiviral Activity and Transport Across Rabbit Cornea Materials and Methods Materials Val-ACV was a gift from Glaxo Wellcome Inc, Research Triangle Park, N.C. [$^3$H] Glycylsarcosine (specific activity 4 Ci/mmol) and [$^3$H] Valacyclovir (Val-ACV) (specific activity 4 Ci/mmol) were obtained from Moravek Biochemicals, Brea, Calif. [$^{14}$C] Mannitol was obtained from ICN Biochemicals Inc., Irvine, Calif. All other chemicals were obtained from Sigma Chemical Company (St. Louis, Mo.). The solvents were of analytical grade and obtained from Fisher Scientific (St. Louis, Mo.). The dipeptide ACV derivatives namely Val-Val-ACV, Gly-Val-ACV, Val-Tyr-ACV, and Tyr-Val-ACV were synthesized in our laboratory.

Animals

Adult Male New Zealand albino rabbits weighing between 2-2.5 kg were obtained from Myrtle's rabbitry, TN. This research was conducted strictly according to the principles embodied in the declaration of Helsinki and The Guiding Principles in the Care and Use of Animals (DHEW Publication NIH 80-23).

Chemical Stability Studies

Six pH values, 1.2, 2.6, 4.2, 5.6, 7.4 and 9.0 were selected. HCl (pH 1.2 & 2.6), phthalate (pH 4.2 & 5.6), phosphate (pH 7.4) and boric acid (pH 9.0) buffers were prepared and ionic strength was adjusted at 0.1 M. The electrode was calibrated at room temperature and pH of the buffers was measured before each study. Stock solutions of the ACV derivatives (1 mM) were prepared and used immediately for stability studies. Aliquots (9.8 ml) of the buffer were placed in a screw-capped vial and allowed to equilibrate at 37° C. ACV derivative stock solution (0.2 ml) was subsequently added to the buffer. The vials were placed in a constant shaker bath set at 37° C. and 60 rpm. Samples (0.2 ml) were collected at appropriate time intervals for up to 7 days. The samples were immediately stored at −80° C. During analysis the samples were thawed and immediately analyzed. All experiments were conducted at least in triplicate.

Ocular Tissue Homogenate Studies

Preparation of Ocular Tissues:

New Zealand albino male rabbits were used for this study. Animals were euthanized by a lethal injection of sodium pentobarbital through the marginal ear vein. Each eye was immediately enucleated and the ocular surface was rinsed with ice cold pH 7.4 phosphate buffer to remove any trace of blood. After a small incision to the sclera, vitreous humor was aspirated using a 1 ml tuberculin syringe. The cornea, lens and iris ciliary body were sequentially removed after cutting along the scleral-limbus junction and all tissues were stored at −80° C. prior to use. The tissues were homogenized in 5 ml chilled (4° C.) DPBS for about 4 min with a tissue homogenizer Tissue Tearor Model 985-370) in an ice bath. Subsequently the homogenates were centrifuged at 12,500 rpm for 25 min at 4° C. to remove cellular debris and the supernatant was used for hydrolysis studies. Protein content of each supernatant was determined with a BioRad assay using bovine serum albumin as the standard.

Hydrolysis Procedure:

The supernatant was equilibrated at 37° C. for about 30 min prior to an experiment. Hydrolysis was initiated by the addition of 0.2 ml of a 1 mM ACV derivative solution to 0.8 ml of the supernatant. The control consisted of 0.8 ml of DPBS instead of the supernatant. Aliquots (50 µl) were withdrawn at appropriate time intervals for up to twenty-four hours. The samples were immediately diluted with 50 µl chilled acetonitrile:methanol (4:5 mixture) to precipitate the proteins and stored at −80° C. until further analysis. The samples were then thawed and centrifuged at 10,000 rpm for 10 min prior to analysis by HPLC for the intact ester ACV derivative and the regenerated ACV. Apparent first order rate constants were calculated and corrected for any chemical hydrolysis observed with the control.

Cell Proliferation Assay

A cell proliferation assay was carried out to examine the toxicity of TFT in comparison to the newly synthesized dipeptide esters of ACV. For this assay CellTiter 96® AQ$_{ueous}$ Non-Radioactive Cell Proliferation Assay Kit™ (Promega, Madison, Wis.) was used. This assay is a calorimetric method for determining the number of cells in proliferation. Studies were carried out to examine comparative toxicities of TFT and the dipeptide ACV derivatives in SIRC cells, which were plated at passage 410 in 96 well plates. Solutions of TFT and the various ACV derivatives (5 mM) were made in the culture medium and appropriate volumes were added to make up to a final volume of 100 µl medium in each well. The cells were incubated along with the drug solution in a humidified 5% $CO_2$ atmosphere. Inhibitory effect of the compounds on the proliferation of these cells was observed. Also the concentration dependent effect of TFT, ACV and Val-Val-ACV on the viability of cells was assessed. The proliferation of SIRC cells in the presence of different concentrations of TFT and the compounds was compared with the positive control (without drug) at each time point and these values were all corrected for, using a negative control (without cells).

Antiviral Testing

The in vitro potency of the parent drug, ACV and Val-ACV, Val-Val-ACV, Gly-Val-ACV and Val-Tyr-ACV were determined against various Herpes viruses. The compounds were screened against HSV-1, HSV-2, HCMV and VZV. Low passage human fibroblast foreskin cells (HFF) were used at a concentration of $2.5 \times 10^6$ cells per ml in 0.1 ml of minimum essential medium supplemented with 10% fetal bovine serum were used. For HSV-1 and HSV-2, 1000 plaque forming units (PFU) per well were used. CMV and VZV were used at a concentration of 2500 PFU per well. All studies were conducted at NIAID by Dr. Earl Kern at the University of Alabama.

Corneal Permeation Studies

Permeation of ACV, its amino ester L-Val-ACV and dipeptide esters was studied using Side-bi-side™ diffusion cells (type VSC-1, Crown Glass Company Inc.). New Zealand albino rabbits were used for determination of in vitro corneal permeability. The rabbits were euthanized by injecting an overdose of pentobarbital into the marginal ear vein. The eyes were proptosed and immediately enucleated followed by washing with ice-cold Dulbecco's Phosphate Buffer Saline (DPBS) to remove any trace of blood. The cornea was removed in a similar fashion as described in the preparation of ocular tissues section previously, except that some scleral portion was left adhered to the cornea, which helped to secure the membrane in place between the half-cells during the course of a transport study. After removal the cornea was washed with ice cold DPBS and mounted on the side-bi-side diffusion half cell with the epithelial side facing the donor chamber. Temperature of the half-cells was maintained at 34° C. by circulating water through the jacketed chambers of the diffusion apparatus. DPBS (3.2 ml) was added to the receiver chamber and the other half chamber (donor chamber) was filled with appropriate drug or ACV derivative solutions (3 ml). A slightly excess volume in the receiver chamber helped to maintain the corneal shape by a marginally elevated hydrostatic pressure. The contents of both the chambers were stirred continuously with magnetic stirrers. Aliquots (100 µl) were removed from the receptor chamber at appropriate time points over a three-hour period and were replaced with an equal volume of DPBS. The samples were stored at −80° C. until further HPLC analysis.

Control experiments using [$^{14}$C] mannitol, a paracellular marker were carried out in a similar way to assess corneal integrity during the course of the experiment.

Inhibition of Transport Studies

Transport of Val-ACV (1 mM) in presence of 10 mM concentrations of tetraethylammonium (TEA) and para-aminohippuric acid (PAH) was studied to determine the role of the organic anion and organic cation transporters on the transport of Val-ACV. Passage of [$^3$H] Val-ACV (0.5 µCi/ml) across cornea in the absence and presence of various ACV amino acid and dipeptide esters (10 mM)-Val-ACV, Val-Val-ACV, Gly-Val-ACV, Val-Tyr-ACV and Tyr-Val-ACV was also studied in order to ascertain whether these ACV derivatives are recognized by the oligopeptide transporter and thus share the same transporter.

Steady State Flux and Permeability Measurements Across Intact Rabbit Cornea

Steady State Fluxes (SSF) were determined from the slope of the cumulative amount of drug transported versus time graph and expressed per unit of corneal surface area as described by Eq. 8. The cumulative amount of drug transported is the sum of the ACV derivative and the regenerated ACV in the receiver chamber.

$$\text{Flux } (J) = (dM/dt)/A \qquad \text{Eq. 8}$$

M is the cumulative amount of drug transported and A is the corneal surface area exposed to permeant. Corneal membrane permeabilities (CMP) are determined by normalizing the SSF to the donor concentration, $C_d$ according to Eq. 9.

$$\text{Permeability } (P_{app}) = \text{Flux}/C_d \qquad \text{Eq. 9}$$

Analytical Procedures

All non radiolabeled samples were assayed using HPLC. The system comprised of a Rainin Dynamax Pump SD-200, Rainin Dynamax UV Detector UV-C at 254 nm, a HP 1100 series Fluorescence Detector at ex λ=285 nm, em λ=370 nm and an Alcott autosampler Model 718 AL HPLC. The column used was a C18 Luna column 4.6×250 mm (Phenomenex). The mobile phase consisted of a mixture of buffer and an organic modifier. The percentage of organic phase was varied in order to elute compounds of interest. This method gave rapid and reproducible results.

HPLC conditions for the various compounds have been summarized in Table 1. For radiolabeled samples from transport studies aliquots (100 µl) for each time point were transferred to scintillation vials containing 5 ml scintillation cocktail (Fisher Scientific, Fairlawn, N.J.). Samples were then analyzed by the liquid scintillation spectrophotometry using scintillation counter (Beckman Instruments Inc., Model LS-6500).

Statistical Analysis

All experiments were conducted at least in triplicate and the results are expressed as mean±SD. Student's t-test was used to detect statistical significance and $p<0.05$ was considered to be statistically significant.

Results

Chemical Stability of ACV Derivatives

The chemical stability experiments revealed that the dipeptide esters of ACV were more unstable in alkaline pH than in acidic pH. All the dipeptide esters did not show any measurable degradation at pH 5.6 during a 7-day experiment and were thus more stable than Val-ACV ($t_{1/2}$~72 hrs.) at pH 5.6. The dipeptide esters, Val-Val-ACV and Gly-Val-ACV were more stable than Val-ACV in a pH range of 1.2-9.0 (except for Gly-Val-ACV at pH, 9.0). The dipeptide ACV esters were found to be more soluble than the parent drug ACV. The solubility of the ACV derivatives ranged from 15-30 mg/ml at 25° C.

Ocular Tissue Bioreversion

Figure 18A:
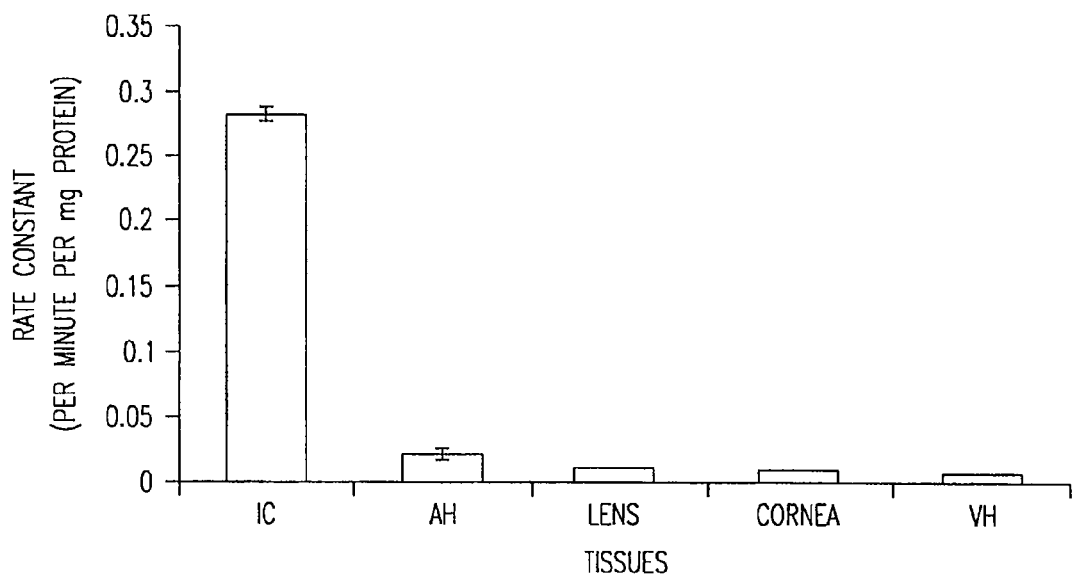
FIG. 18 shows a comparison of the hydrolytic rate constants for (panel A) L-Val-ACV and (panel B) Val-Val-ACV in various ocular tissue homogenates: Cornea, Iris Ciliary Body (IC), Aqueous Humor (AH), Vitreous Humor (VH), and Lens. (Mean±S.D., n=3).
Figure 18B:
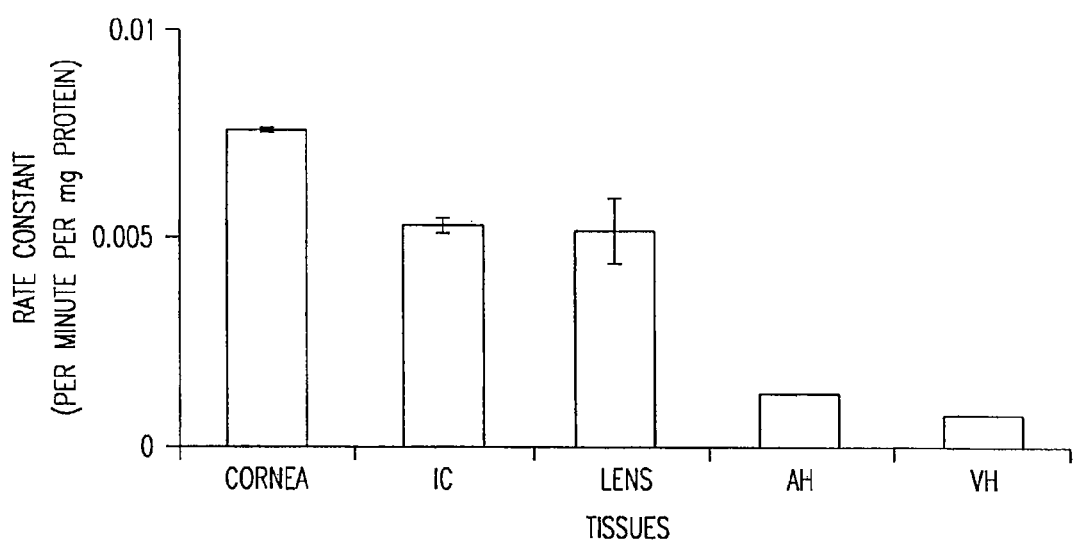

Enzymatic hydrolysis of the ACV derivatives was assessed using the ocular tissues. All the ACV derivatives hydrolyzed to yield the active parent drug, ACV. A tabulated account of the hydrolytic rate constants of the various ACV derivatives in various ocular tissues is listed in Table 3. The enzyme hydrolytic rate constants have been calculated after subtracting the contribution due to chemical hydrolysis (DPBS pH 7.4). The L-valyl ester ACV derivative of ACV was readily converted to the active parent drug, ACV ($t_{1/2}$~85 min.) in corneal tissue homogenate (FIG. 18, panel A). Also Val-Val-ACV was hydrolyzed to the parent drug, ACV ($t_{1/2}$~93 min.) upon sequential hydrolysis to Val-ACV (FIG. 18, panel B). FIG. 18, panels A and B, highlight the varied susceptibility of Val-ACV and Val-Val-ACV to various ocular tissues. Scheme 3 depicts the mechanism of regeneration of ACV from Val-Val-ACV following enzymatic hydrolysis in corneal tissue. The hydrolysis is mainly enzymatic and not chemical as Val-Val-ACV is relatively more stable in DPBS (pH 7.4, $t_{1/2}$=108 hours) as compared to corneal tissue homogenate ($t_{1/2}$=1.4 hours).

TABLE 13

Ocular Tissue Hydrolysis of Esters of ACV

| Drug | Cornea | Aqueous Humor | Lens | Iris-Ciliary Body | Vitreous Humor |
|---|---|---|---|---|---|
| Val-ACV | 8.1 (±1.2) | 21.8 (±1.2) | 10.1 (±0.3) | 283.1 (±19.7) | 7.1 (±0.9) |
| Val-Val-ACV | 7.5 (±0.03) | 1.3 (±0.1) | 4.5 (±0.7) | 5.2 (±0.18) | 0.8 (±0.02) |
| Gly-Val-ACV | 2.7 (±0.29) | 7.8 (±0.34) | 1.69 (±0.19) | 5.8 (±0.22) | 0.35 (±0.01) |
| Tyr-Val-ACV | 4.9 (±0.69) | 2.3 (±0.11) | 3.1 (±0.63) | 5.3 (±0.74) | 1.7 (±0.56) |
| Val-Tyr-ACV | 5.8 (±0.42) | 1.9 (±0.91) | 3.6 (±0.52) | 4.1 (±0.71) | 1.1 (±0.45) |

Values are represented as $k \times 10^3 \text{ min}^{-1} \text{ mg}^{-1}$ protein
Values are Mean ± S.D. (n = 3)

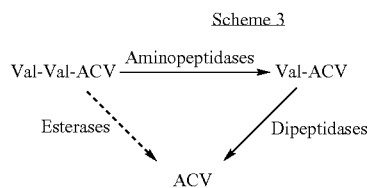

Scheme 3

Cell Proliferation Assay

Figure 19:
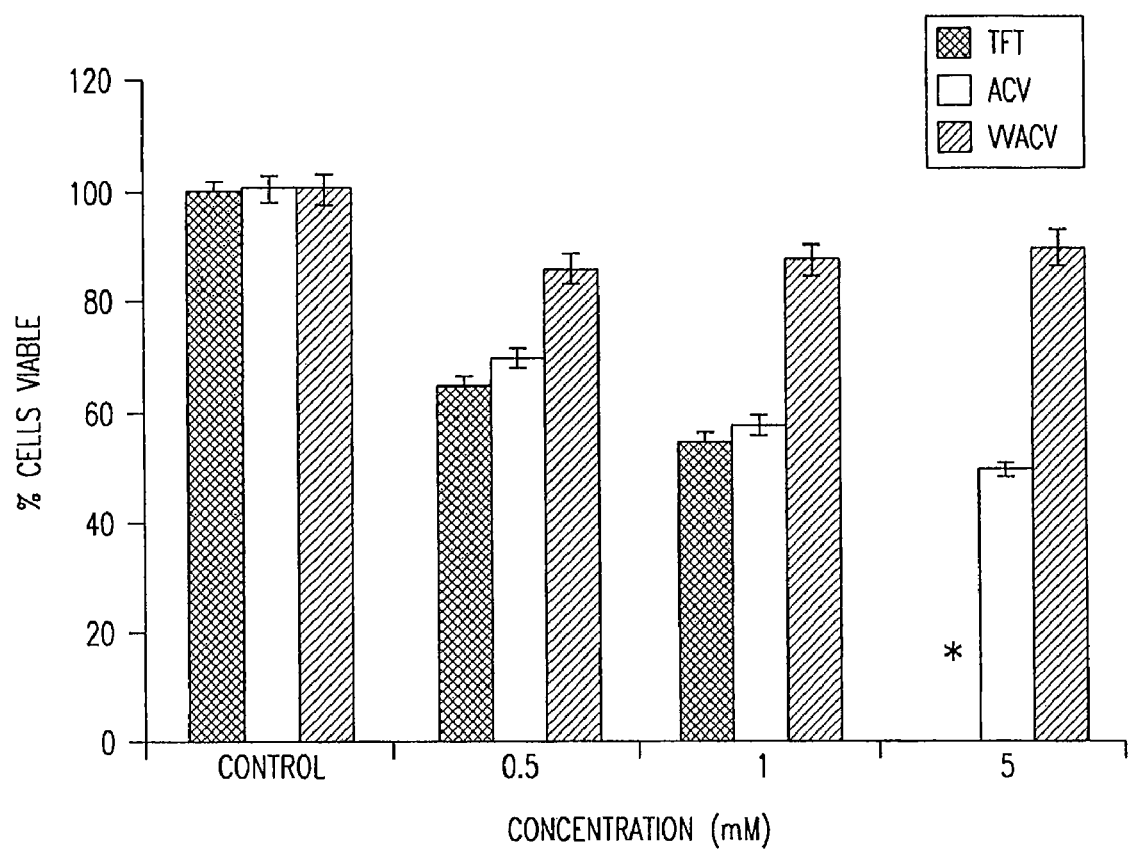
FIG. 19 shows the percentage cells viable in the presence of 0.5, 1, and 5 mM concentrations of TFT, ACV and Val-ACV. * Denotes almost complete cell death (0.01%) in presence of 5 mM concentration of TFT. (Mean±S.D., n=3.)

The results indicated that TFT inhibited cell growth in a concentration dependent manner. ACV also inhibited growth but to a much lesser extent. TFT caused complete cell death (0.01% viable) at and above 5 mM. The dipeptide esters of ACV were screened for cytotoxicity and showed no significant cell growth inhibition up to 5 mM concentrations up to a period of 48 hrs. The % viable cells calculated in presence of 5 mM concentrations of various drugs were found to be: TFT, 0.01±0.1; ACV, 49.1±4.2; Val-ACV, 89.3±5.1; Val-Val-ACV, 90.1±4.6; Gly-Val-ACV, 81.1±6.7; Val-Tyr-ACV, 80.2±6.2. The toxicity of TFT, ACV and Val-Val-ACV was found to be concentration dependent (FIG. 19).

In Vitro Antiviral Screening

The dipeptide esters of ACV exhibited excellent in vitro antiviral efficacy against HSV1. These ACV derivatives are themselves inactive and undergo hydrolysis to yield the active parent drug, acyclovir. Val-Val-ACV and Val-Tyr-ACV showed excellent antiviral activity against HSV-1 with an $EC_{50}$ of 6.14 μM and 4.8 μM respectively in comparison to 7.1 μM with ACV and 9.1 μM with Val-ACV. The $CC_{50}$ for HSV-1 ranged from 166-186 μM for the dipeptide ACV derivatives and the selectivity index (SI) of Val-Val-ACV (30.3) and Val-Tyr-ACV (34.4) was found to be comparable to Val-ACV (30.3). However the Selectivity index of VZV for the dipeptide ACV esters ranged from 417-2000 in comparison to 3333 for Val-ACV (Table 14).

TABLE 14

In vitro Antiviral Activity of Derivatives of ACV

| Entity | HSV-1 (μM) CPE Inhibition | HSV-2 (μM) CPE Inhibition | HCMV (μM) CPE Inhibition | VZV (μM) CPE Inhibition | EBV (μM) VCA Elisa |
|---|---|---|---|---|---|
| ACV | $EC_{50} = 7.1$ | $EC_{50} = 6.6$ | — | $EC_{50} = 0.53$ | $EC_{50} = 7.5$ |
| GCV | — | — | $EC_{50} = 0.94$ | — | — |
| Val-ACV | $EC_{50} = 9.1$ | $EC_{50} = 7.77$ | $EC_{50} = 30.8$ | $EC_{50} < 0.08$ | $C_{50} = 0.55$ |
| | $CC_{50} > 277$ | $CC_{50} > 277$ | $CC_{50} > 277$ | $CC_{50} > 100$ | $CC_{50} > 138$ |
| | SI > 30.3 | SI > 35.7 | SI > 9 | SI > 3333 | SI > 250 |
| Val-Val-ACV | $EC_{50} = 6.14$ | $EC_{50} = 22.7$ | $EC_{50} > 186$ | $EC_{50} = 0.09$ | $EC_{50} = 93.1$ |
| | $CC_{50} > 186$ | $CC_{50} > 186$ | $CC_{50} > 186$ | $CC_{50} > 186$ | $CC_{50} > 93.1$ |
| | SI > 30.3 | SI > 8.2 | SI > 0 | SI > 2000 | SI > 0 |
| Gly-Val-ACV | $EC_{50} = 12.6$ | $EC_{50} = 22.7$ | $EC_{50} = 59.5$ | $EC_{50} = 0.38$ | $EC_{50} = 5.61$ |
| | $CC_{50} > 160$ | $CC_{50} > 160$ | $CC_{50} > 160$ | $CC_{50} > 16$ | $CC_{50} > 80.1$ |
| | SI > 12.6 | SI > 5.8 | SI > 2.6 | SI > 417 | SI > 14.2 |
| Val-Tyr-ACV | $EC_{50} = 4.8$ | $EC_{50} > 25.1$ | $EC_{50} = 56.8$ | $EC_{50} = 0.16$ | $EC_{50} = 50.2$ |
| | $CC_{50} > 166$ | $CC_{50} > 166$ | $CC_{50} > 166$ | $CC_{50} > 166$ | $CC_{50} > 83.1$ |
| | SI > 34.4 | SI > 6.6 | SI > 2.9 | SI > 1000 | SI > 1.6 |

Figure 20:
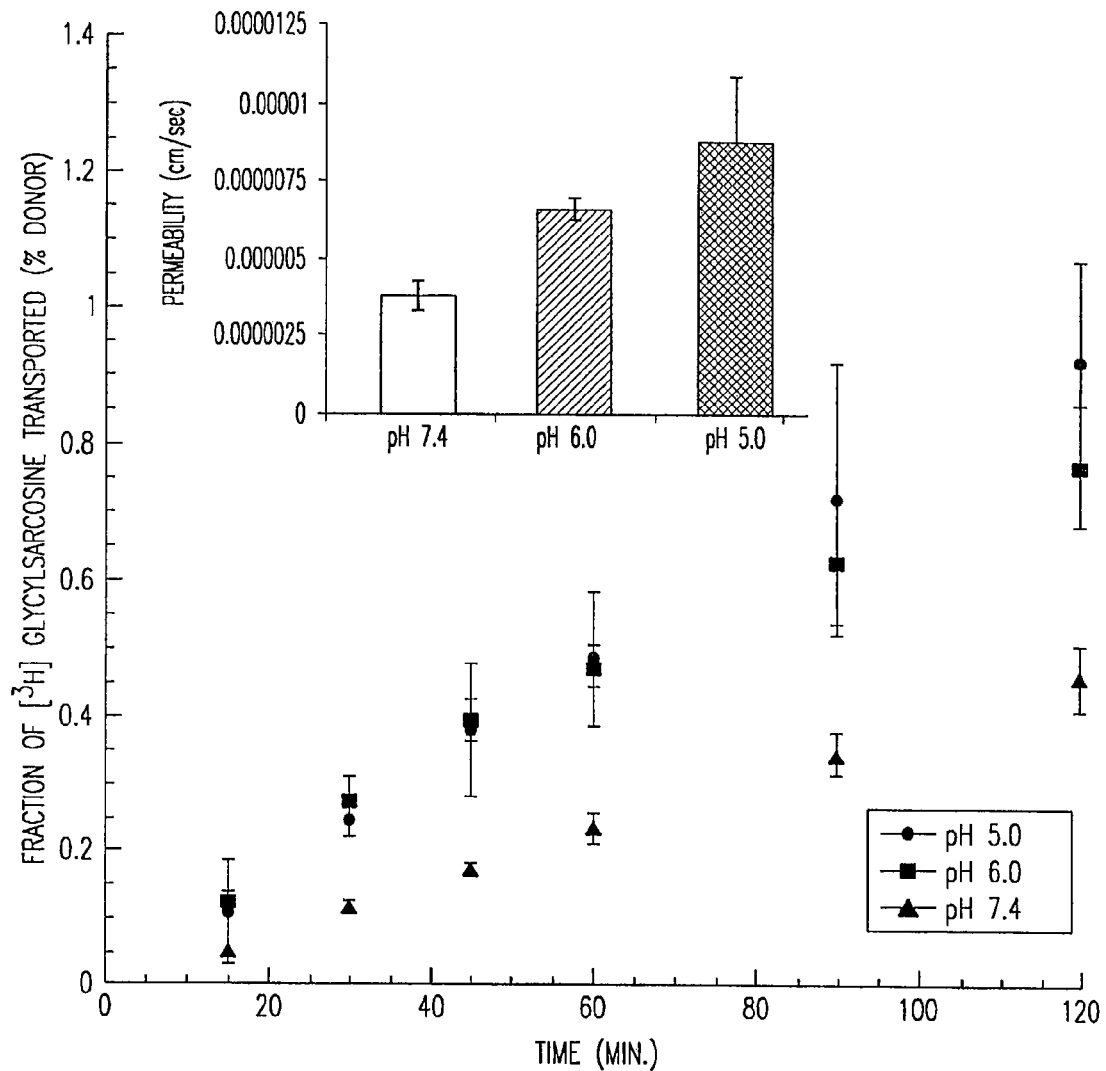
FIG. 20 is a graph of the transport of [$^3$H] Glycylsarcosine into rabbit cornea at (▲) pH 7.4 (■) pH 6.0 (♦) pH 5.0. Inset, comparison of permeabilities (cm/sec) of [$^3$H] Glycylsarcosine at different pH's. (Mean±S.D., n=3-6).
Figure 21A:
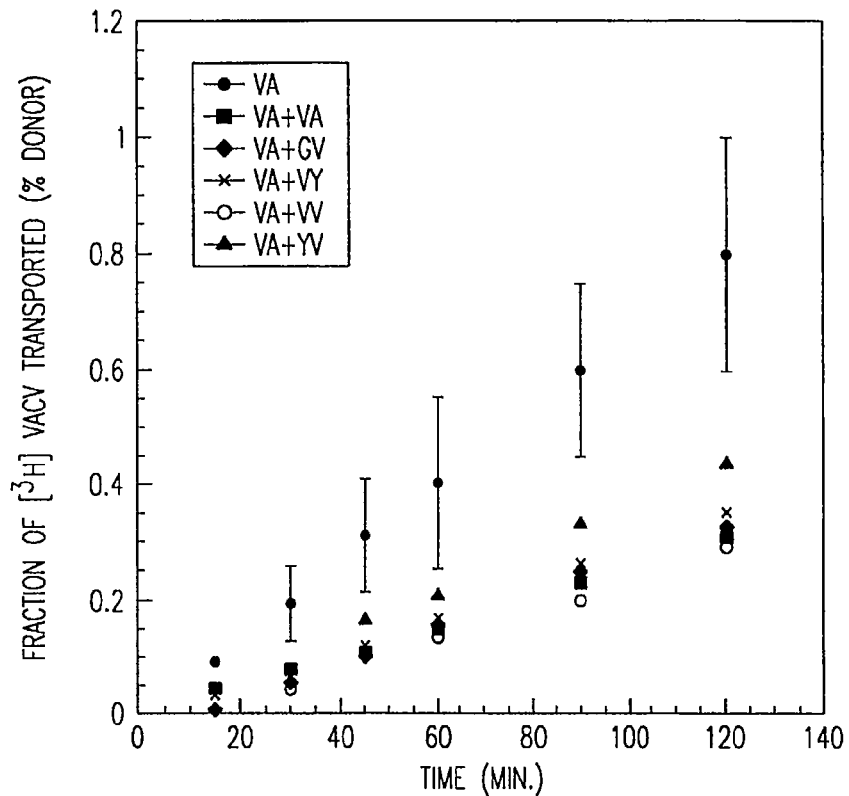
FIG. 21. Panel A is a graph of the time course of transport of (●) [$^3$H] Val-ACV in presence of 10 mM (■) Val-ACV, (♦) Gly-Val-ACV, (X) Val-Tyr-ACV, (+) Val-Val-ACV, (Δ) Tyr-Val-ACV across isolated rabbit cornea. (Error bars have not been included for clarity). Panel B shows the time course of the cumulative amount of (●) ACV (R$^2$=0.996) and (■) L-Val-ACV (R$^2$=0.991) (▲) Val-Val-ACV (R$^2$=0.995) penetrating the rabbit cornea. (Mean±S.D., n=3-6).
Figure 21B:
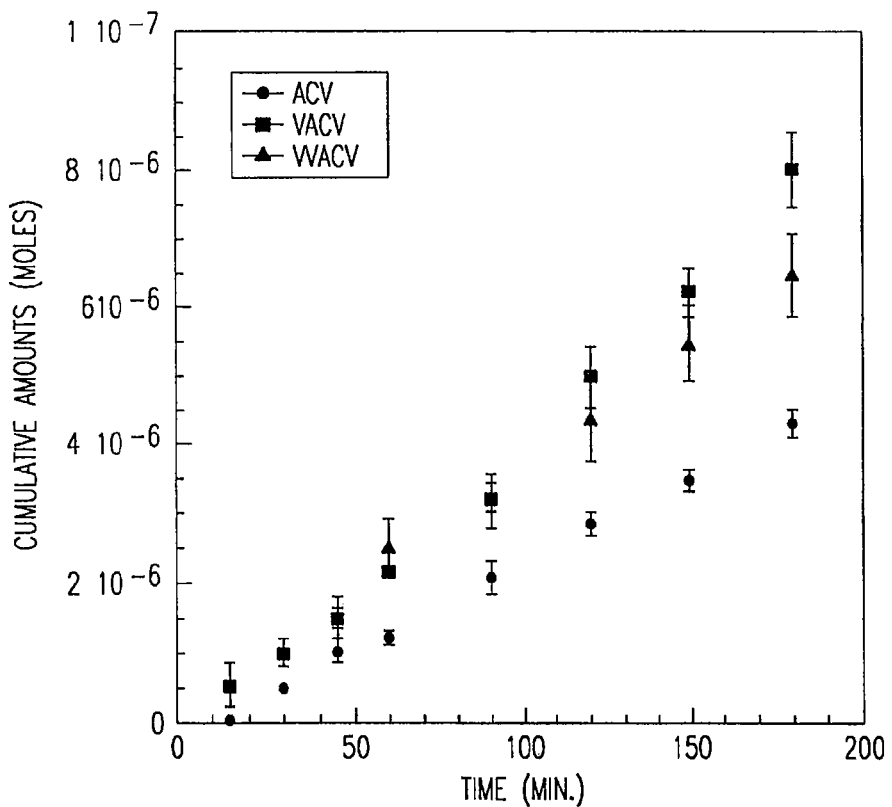

$EC_{50}$ is the concentration required to inhibit viral cytopathogenicity by 50%.
$CC_{50}$ is the concentration required to inhibit cell proliferation by 50%.
SI (Selectivity Index) = $CC_{50}/EC_{50}$ Transport Experiments The pH dependent transport of Gly-Sar across cornea was assessed (FIG. 20). Also the transport of 1 mM Val-ACV in the presence of PAH and TEA was assayed in order to delineate the involvement of any other transporters in the absorption of Val-ACV. The transport of Val-ACV in the absence (control) and presence of PAH and TEA (percent of control) was found to be 100±2.3, 99.6±2.6 and 101.3±1.1 respectively. All ACV derivatives hydrolyzed to yield the parent drug, ACV during the transport experiments. Therefore the total amount of drug permeating through the corneal membrane was taken as the sum of the intact ACV derivative, the regenerated amino acid intermediate (in case of dipeptide esters) and the parent ACV. The dipeptide esters of ACV inhibited the transport of [$^3$H] Val-ACV, a derivative extensively studied for its affinity to the oligopeptide transporters (Table 15, FIG. 21, panel A). The corneal permeability of [$^3$H] Val-ACV was 10.7±0.9×10$^{-6}$ cm/sec in comparison to 2.01–3.34×10$^{-6}$ cm/sec in presence of 10 mM concentration of unlabeled Val-ACV and dipeptide esters of ACV. FIG. 21, panel B, depicts the time course of transport of cumulative amount of ACV, Val-ACV regenerated and Val-Val-ACV transported on transport of 1 mM Val-Val-ACV across cornea. The dipeptide esters of acyclovir exhibited higher permeabilities across cornea than the parent drug (Table 15) suggesting the involvement of the oligopeptide transporter in mediating their absorption across cornea. Scheme 3 depicts the breakdown of Val-Val-ACV following transport across corneal membrane.

TABLE 15

Inhibition of Transport of [$^3$H] Val-ACV in presence of esters of ACV. Permeability of esters across freshly excised rabbit cornea

| Drug | |
|---|---|
| | $P_{app}$ (% Control) (± S.D) |
| [$^3$H] Val-ACV | 100 (±8.5)$^a$ |
| +10 mM Val-ACV | 20.1 (±6.7)* |
| +10 mM Val-Val-ACV | 18.6 (±8.9)* |
| +10 mM Gly-Val-ACV | 23.7 (±6.6)* |
| +10 mM Val-Tyr-ACV | 23.4 (±7.7)* |
| +10 mM Tyr-Val-ACV | 31.1 (±9.5)* |
| | $P_{app}$ * 10$^6$ cm/sec (± S.D) |
| ACV | 4.24 (±1.41)$^b$ |
| Val-ACV | 12.1 (±0.44)* |
| Val-Val-ACV | 9.91 (±2.40)* |
| Gly-Val-ACV | 12.4 (±1.42)* |
| Tyr-Val-ACV | 7.19 (±1.38)* |
| Val-Tyr-ACV | 8.34 (±1.12)* |

$^{a,b}$control
*p < 0.05

Discussion

The L-valyl ester of ACV exhibited a higher corneal permeability and higher bioavailability on oral absorption than ACV due to its recognition by the oligopeptide transporter on the cornea and intestine respectively. Although the utility of valacyclovir against oral and genital herpes infections is well established, it has not been used for topical application against ocular herpes infection probably due to a short half life ~72 hours in pH 5.6 buffer at 37° C. (Table 12). For this reason it cannot be formulated into aqueous eye drops, which should be stable for 2-3 years. In comparison the dipeptide derivatives exhibit increased solution stability in the pH range studied with no measurable degradation in pH 5.6 during a 7 day experiment (Table 2) thereby allowing the aqueous formulation to be stable for a longer period. All the dipeptide derivatives studied showed no measurable degradation at pH 5.6 during a seven-day experiment, which makes them feasible for formulation into stable aqueous eye drops. The dipeptide ACV derivatives have also shown high solubility, 15-30 mg/ml at 25° C., as compared to 2.5 mg/ml for ACV, thereby allowing formulation into 1-3% stable eye drops. Application of such high concentrations of dipeptides esters of ACV may also eradicate stromal infection, which is not adequately treated by current antiviral therapeutic regimens.

These dipeptide ACV derivatives hydrolyze to regenerate the active parent drug, ACV, in various ocular tissues. FIG. 18 panels A and B depict the susceptibility of Val-ACV and Val-Val-ACV respectively to the enzymatic hydrolysis in various ocular tissues. In the case of Val-ACV, maximum hydrolysis is evident in the iris ciliary body (FIG. 18 panel A), which is vascularized and contains higher amount of esterases (Hughes et al., J. Ocul. Pharmacol. 9:287-297 (1993)). The absence of any other metabolite during hydrolysis of Val-ACV other than the parent drug, ACV (FIG. 18 panel A) depicts true esterase activity. The trend of hydrolysis for Val-Val-ACV which decreases from cornea to iris ciliary body to lens to aqueous humor (FIG. 18 panel B) matches the profile of presence of aminopeptidases in ocular tissues which decreases from cornea to iris ciliary body to lens to aqueous humor (Stratford, R. E., et al., Curr. Eye Res. 4:995-999 (1985)). The aminopeptidase-mediated enzymatic breakdown of Val-Val-ACV is evident from the formation of Val-ACV during corneal hydrolysis (FIG. 18 panel B). All the other dipeptides were also susceptible to the ocular enzymes with corneal half-lives ranging from 1.54-4.27 hrs in comparison to 1.42 hrs for Val-ACV.

The antiviral efficacy of the ACV derivatives was tested against HSV 1 & 2, CMV, VZV and EBV (Table 14). The drugs were found to be particularly effective against HSV 1 and VZV. Two compounds, Val-Val-ACV and Val-Tyr-ACV, were found to be the most effective against HSV-1. The selectivity index of both the compounds was comparable to that of Val-ACV and therefore these drugs are highly selective and effective against the infected cells. The SI of the ACV derivatives against VZV was also very high and therefore these drugs could be further tested and developed for infections caused by VZV. Also Val-ACV and Gly-Val-ACV showed antiviral activity against EBV and therefore could be promising drug candidates in diseases caused by EBV. ACV and the ACV derivatives were inactive towards CMV with very high EC$_{50}$ values (Table 14).

The mechanism of corneal permeation of the dipeptide ACV derivatives was delineated by performing inhibition and transport experiments with freshly isolated rabbit cornea. Transport of Val-ACV in the presence of [$^3$H] Val-ACV was assessed in presence of the various ACV derivatives. Val-ACV was chosen as it has been previously reported that its transport across cornea is efficiently mediated by the oligopeptide transporter present on the rabbit cornea. Moreover the lack of Val-ACV interaction with an organic cation, tetraethylammonium, and an organic anion, para-aminohippuric acid, suggests the absence of any appreciable corneal transport activity due to the organic cation and organic anion transporters, probably due to the absence of the transporter on the cornea or due to the concentration (1 mM) at which the transport was assessed. Therefore the inhibition of transport of [$^3$H] Val-ACV (Table 15, FIG. 21 panel A) across cornea probably indicates an interaction of the newly synthesized dipeptide esters of ACV with the oligopeptide transporter.

The permeability of dipeptide esters ($7.19\text{-}12.4\times10^{-6}$ cm/sec) was also found to be comparable to that of Val-ACV ($12.1\pm0.44\times10^{-6}$ cm/sec) and significantly ($p<0.05$) higher than that of the parent drug, ACV ($4.24\pm1.41\times10^{-6}$ cm/sec) confirming the role of the oligopeptide transporter in the passage of these dipeptide esters across rabbit cornea. It was noticed during the transport experiments that the dipeptide esters hydrolyzed to yield the parent ACV via the amino acid intermediate ACV derivative albeit in a very small amount. Since the contribution from the chemical hydrolysis was significantly lower compared to the enzymatic breakdown owing to the enzymes in the intact corneal tissue, it was evident that the ACV derivative primarily hydrolyzed enzymatically.

In summary, the dipeptide esters of ACV were designed and evaluated as possible drug candidates against HSV keratitis. The overall aim was to improve ocular bioavailability of ACV upon recognition of the dipeptide esters by the oligopeptide transporter on the cornea. The dipeptide esters of ACV have shown excellent activity against herpes virus. Also these esters exhibit excellent solution stability and much less cytotoxicity as compared to valacyclovir and trifluorothymidine respectively. These dipeptide esters can be formulated into 1-3% eye drops and therefore seem to be promising drug candidates in the treatment of HSV keratitis with stromal involvement, a clinical indication not adequately treated by the current therapy.

Example 13

Pharmacokinetics of Novel Dipeptide Ester Prodrug of Acyclovir Following Oral Administration Intestinal Absorption and Liver Metabolism This example examines the bioavailability of a series of the dipeptide prodrug, Glycine-Valine ACV in comparison to ACV and Val-ACV (VACV) following oral administration in Sprague-Dawley rats with cannulated jugular and portal veins.

1. Methods a. Oral Absorption Studies

Oral absorption studies of ACV, Val-ACV (VACV) and Gly-Val-ACV (GVACV) were carried out at an equivalent dose of 20.0 mg/kg. Animals were fasted overnight (12-18 h) with free access to water. Drug solutions were administered by oral gavage (0.8 ml). Blood samples (200 µl) were collected from the jugular and portal veins at predetermined time intervals over a period of 4 h. Heparinized saline (200 µl) was injected through both the veins in order to maintain a fairly constant fluid volume. Plasma was immediately separated by centrifugation and then stored at −80° C. until further analysis.

Plasma samples were thawed at room temperature and 0.2 ml of methanol was added to 0.2 ml of plasma in an eppendorf tube. The mixture was vortexed for 30 sec. and centrifuged at 10,000 rpm for 10 minutes at 4° C. The supernatant was then separated and an aliquot was directly injected onto the column for HPLC analysis.

b. Statistical Analysis

All experiments were conducted at least in triplicate and results are expressed as mean±SD. All relevant pharmacokinetic parameters were calculated using non-compartmental analyses of plasma-time curves following oral administration of ACV, VACV and GVACV using a pharmacokinetic software package, Win Nonlin, v2.1 (Pharsight, Calif.). Maximum plasma concentrations ($C_{max}$) were obtained from the plasma-concentration time curves and the area under the plasma concentration time curves ($AUC_{0\text{-}last}$ and $AUC_{0\text{-}inf}$) were determined by the linear trapezoidal method with extrapolation. The slopes of the terminal phase of plasma profiles were estimated by log-linear regression and the terminal rate constant ($\lambda_z$) was derived from the slope. The terminal plasma half-lives were calculated from the equation: $t_{1/2}=0.693/\lambda_z$.

2. Results a. Intestinal Absorption

Figure 22:
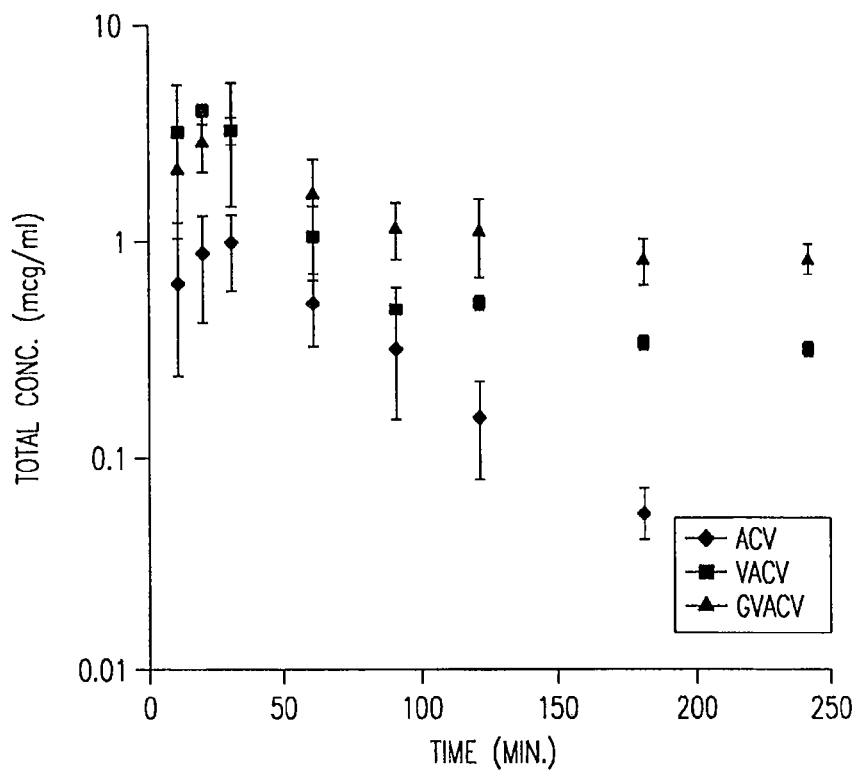
FIG. 22 is a graph of the intestinal transport of ACV, Valacyclovir and Glycine-Valine-Acyclovir upon oral administration.

The comparative intestinal absorption plasma-concentration time profiles of ACV, VACV and GVACV is depicted in FIG. 22. Pharmacokinetic parameters have been summarized in Table 16.

TABLE 16

Pharmacokinetic Parameters following intestinal absorption

| Parameters | ACV | VACV | GVACV |
|---|---|---|---|
| $AUC_{(0\text{-}t)(TC)}$ (min µg ml$^{-1}$) | 21.2 ± 5.2 | 208.4 ± 41.2 | 416.1 ± 140.9 |
| $AUC_{inf(TC)}$ (min µg ml$^{-1}$) | 27.9 ± 6.1 | 237.9 ± 51.8 | 598.7 ± 164.1 |
| $C_{max(TC)}$ (µg ml$^{-1}$) | 0.89 ± 0.18 | 4.53 ± 0.95 | 4.07 ± 1.03 |
| $T_{max(TC)}$ (min) | 24.0 ± 8.9 | 22.5 ± 5.0 | 21.4 ± 5.77 |
| $C_{last(TC)}$ (µg ml$^{-1}$) | 0.05 ± 0.01 | 0.3 ± 0.003 | 0.81 ± 0.12 |
| $AUC_{(0\text{-}t)(ACV)}$ (min µg ml$^{-1}$) | 21.2 ± 5.2 | 246.2 ± 82.2 | 347.8 ± 108.2 |
| $AUC_{(0\text{-}t)(AA)}$ (min µg ml$^{-1}$) | — | 19.07 ± 2.5 | 143.6 ± 51.4 |
| $C_{max(ACV)}$ (µg ml$^{-1}$) | 0.89 ± 0.18 | 4.86 ± 1.51 | 4.06 ± 1.44 |
| $C_{max(AA)}$ (µg ml$^{-1}$) | — | 0.41 ± 0.2 | 0.99 ± 0.54 |
| $Cl_{(ACV)}$ (ml min$^{-1}$) | 38.5 ± 8.7 | 17.6 ± 6.6 | 12.5 ± 5.5 |
| $Cl_{(AA)}$ (ml min$^{-1}$) | — | — | 31.9 ± 5.3 |
| $MRT_{(ACV)}$ (min.) | 44.8 ± 5.6 | 62.6 ± 6.6 | 64.1 ± 5.35 |
| $\lambda_{z(ACV)}$ (min$^{-1}$) | 0.015 ± 0.001 | 0.004 ± 0.0001 | 0.005 ± 0.001 |
| $MRT_{AA}$ (min.) | — | 12.6 ± 2.5 | 110.9 ± 18.7 |
| $\lambda_{z(AA)}$ (min$^{-1}$) | — | — | 0.005 ± 0.003 |

Values are mean ± S.D. (n = 3-6);
TC—Total concentration in terms of ACV;
ACV—Acyclovir;
AA—amino acid intermediate.

Oral administration of VACV and GVACV led to an increase in intestinal absorption of ACV as compared to ACV alone. GVACV led to approximately two-fold elevation over VACV.

b. Systemic Absorption

Figure 23:
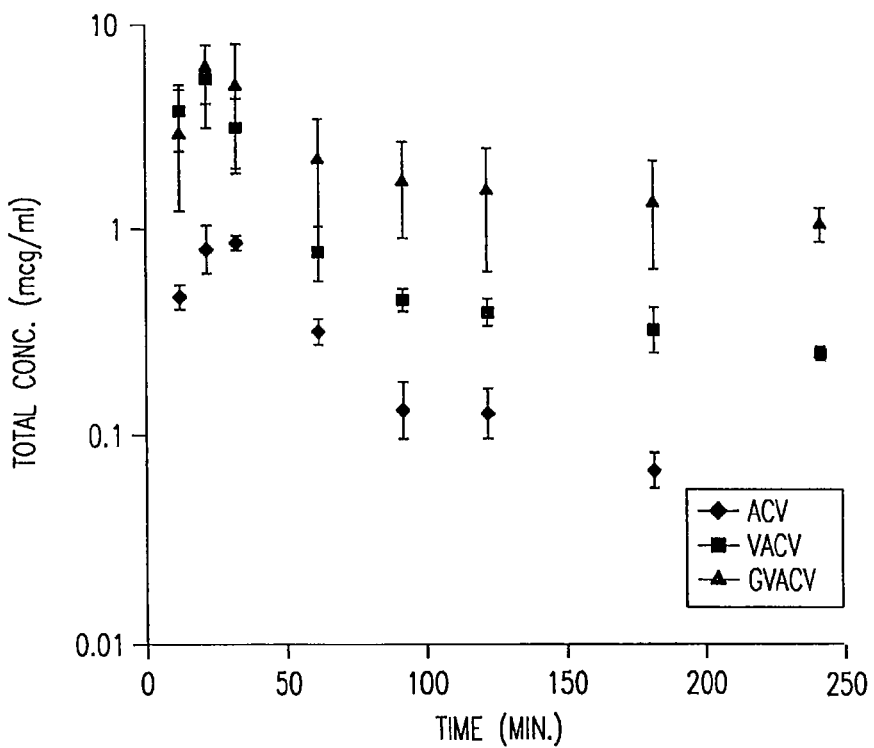
FIG. 23 is a graph of the systemic absorption of Acyclovir, Valacyclovir and Glycine-Valine Acyclovir upon oral administration.

The comparative systemic absorption plasma-concentration time profiles of ACV, VACV and GVACV are depicted in FIG. 23. The pharmacokinetic parameters obtained following administrations of parent ACV and the prodrugs are listed in Table 17. Highest systemic exposure was obtained upon administration of GVACV relative to ACV and VACV.

TABLE 17

Pharmacokinetic Parameters following systemic absorption

| Parameters | ACV | VACV | GVACV |
|---|---|---|---|
| $AUC_{(0\text{-}t)(CC)}$ (min µg ml$^{-1}$) | 20.4 ± 3.8 | 237.1 ± 64.6 | 633.8 ± 115.5 |
| $AUC_{inf(CC)}$ (min µg ml$^{-1}$) | 29.9 ± 4.2 | 288.6 ± 59.4 | 900.7 ± 74.8 |
| $C_{max(CC)}$ (µg ml$^{-1}$) | 0.83 ± 0.19 | 5.44 ± 2.33 | 7.2 ± 3.3 |
| $T_{max(CC)}$ (min) | 24.0 ± 5.4 | 22.0 | 22.2 ± 8.3 |
| $C_{last(CC)}$ (µg ml$^{-1}$) | 0.06 ± 0.01 | 0.25 ± 0.01 | 1.1 ± 0.21 |
| $AUC_{(0\text{-}t)(ACV)}$ | 20.47 ± 3.8 | 232.53 ± 66.04 | 571.68 ± 99.22 |

TABLE 17-continued

Pharmacokinetic Parameters following systemic absorption

| Parameters | ACV | VACV | GVACV |
|---|---|---|---|
| $AUC_{(0-t)\ (AA)}$ (min μg ml$^{-1}$) | — | 15.02 ± 0.48 | 133.1 ± 48.2 |
| $C_{max\ (ACV)}$ (μg ml$^{-1}$) | 0.83 ± 0.19 | 5.30 ± 2.38 | 6.9 ± 1.50 |
| $C_{max\ (AA)}$ (μg ml$^{-1}$) | — | 1.08 ± 0.01 | 1.30 ± 0.89 |
| $Cl_{(ACV)}$ (ml min$^{-1}$) | 50.9 ± 4.9 | 15.5 ± 3.1 | 13.3 ± 3.5 |
| $Cl_{(AA)}$ (ml min$^{-1}$) | — | — | 26.8 ± 4.5 |
| $MRT_{(ACV)}$ (min.) | 45.82 ± 5.31 | 60.36 ± 8.76 | 79.61 ± 10.64 |
| $\lambda_{z(ACV)}$ (min$^{-1}$) | 0.017 ± 0.007 | 0.0052 ± 0.001 | 0.006 ± 0.001 |
| $MRT_{AA}$ (min.) | — | 12.8 ± 0.16 | 73.2 ± 28.9 |
| $\lambda_{z(AA)}$ (min$^{-1}$) | — | — | 0.006 ± 0.002 |

Values are mean ± S.D. (n = 3-6);
TC—Total concentration in terms of ACV;
ACV—Acyclovir;
AA—amino acid intermediate.

3. Conclusions

Oral absorption studies of these ACV, VACV and the dipeptide prodrug GVACV were carried out in Sprague Dawley rats with cannulated jugular and portal veins. After oral administration, VACV is rapidly absorbed from the GIT and nearly completely converted to ACV and L-valine by first-pass intestinal and/or hepatic metabolism. A small amount of ACV is converted to inactive metabolites by aldehyde oxidase and by alcohol and aldehyde dehydrogenase. Neither VACV or ACV is metabolized by cytochrome P450 enzymes. Therefore in order to assess the role of first pass effect due to intestine and liver, intestinal and systemic absorption of the prodrugs was determined by sampling the portal and jugular vein respectively. The samples collected from the portal vein were compared for their parent drug and the metabolite levels with that from the jugular vein in order to establish the role of intestinal and hepatic metabolism.

Upon oral administration of GVACV and VVACV formation of the amino acid intermediate was observed, which was further metabolized to yield ACV. However VVACV rapidly metabolized to ACV, as no intact amino acid intermediate metabolite VACV could be detected. However intermediate metabolite VACV formed after administration of GVACV underwent significant further metabolism in the liver as evident by higher levels of ACV generated following systemic absorption relative to intestinal absorption (Tables 16 and 17). It is highly likely that the enzyme, BPHL, principally responsible for hydrolysis of VACV is present in the liver as well as intestine (X. S. Puente et al., *J. Biol. Chem.*, 270(21), 12926-32 (1995). AUC's (TC) obtained after oral administration of VACV and GVACV were significantly higher (p<0.05) than ACV itself. This increase in bioavailability of ACV upon oral administration has been attributed to the recognition of VACV by intestinal peptide transporter, hPEPT1 that mediates its transport across intestinal epithelium to blood. Also since GVACV show appreciable affinity towards HPEPT1 (B. S. Anand et al., *J. Pharmacol. Exp.*, 304, 781 (2003)), the oral absorption of these prodrugs is also believed to be mediated through the intestinal peptide transporter, hPEPT1. GVACV yielded the highest $AUC_{(CC)}$, which is at least two fold higher than VACV following intestinal as well as systemic absorption. Such enhancement in absorption could be attributed to the similar affinity of VACV and GVACV towards hPEPT1 (B. S. Anand, cited above), which allows it to be absorbed efficiently across the intestinal mucosa. Also upon metabolism of GVACV, VACV is formed, which itself is a substrate of hPEPT1, whereas on the other hand, VACV metabolizes rapidly to form ACV, which is not a substrate of hPEPT1. The plasma elimination half-life of ACV after administration of VACV ranged from 2.2 hrs-2.8 hrs. upon intestinal and systemic absorption.

In conclusion, oral administration of dipeptide ester prodrug of ACV, GVACV lead to an increase in intestinal and systemic absorption of ACV as compared to direct administration of ACV and VACV. Therefore, the dipeptide prodrugs of ACV particularly GVACG may provide a significant therapeutic advantage in the treatment of oral and genital HSV infections and may be considered a considerable improvement over VACV.

Example 14

Representative Pharmaceutical Dosage Forms

The following illustrate representative pharmaceutical dosage forms, containing a compound of formula I ('Compound X'), for therapeutic or prophylactic use in humans.

| | mg/tablet |
|---|---|
| (i) Tablet 1 | |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| | mg/ml |
|---|---|
| (iv) Injection 1 (1 mg/ml) | |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |
| (v) Injection 2 (10 mg/ml) | |
| 'Compound X' (free acid form) | 10.0 |
| Monobasic sodium phosphate | 0.3 |
| Dibasic sodium phosphate | 1.1 |
| Polyethylene glycol 400 | 200.0 |

| | |
|---|---|
| 01 N Sodium hydroxide solution (pH adjustment to 7.0-7.5) | q.s. |
| Water for injection | q.s. ad 1 mL |
| (vi) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |
| (vii) Ophthalmic Solution or Ointment | mg/ml |
| 'Compound X' | 10-100 |
| Vehicle | |
| Optional Ingredients: | |
| Preservative | 0.01-10 |
| Surfactant | 0.01-10 |
| Chelating agent | 0.01-10 |
| Tonicifier | q.s. to achieve tonicity with lacrimal fluid |
| Buffers | q.s. to maintain pH of formulation within 5.0-7.0 |
| Viscosity agents | q.s. to achieve desired formulation viscosity. |

As used herein, q.s. means quantity sufficient.

If possible the ophthalmic solutions and ophthalmic ointments should be made isotonic with the lacrimal fluids. Preservatives that may be used in the ophthalmic solutions and ointments include quaternary ammonium compounds (e.g., benzalkonium chloride), themerosal, parabens and sorbic acid, Chelating agents such as citric acid and preferably disodium EDTA may be used in the ophthalmic solutions and ophthalmic ointments. The chelating agent may also be used to enhance the anti-microbial activity of the primary preservative. Buffers that may be used in the ophthalmic solutions and ophthalmic ointments include acetate, citrate, and borate. Tonicifiers useful in the ophthalmic solutions and ophthalmic ointments include potassium chloride and sodium chloride. Viscosity agents that are useful include the cellulose derivatives, such as hydroxypropylmethyl cellulose. Stabilizing agents, such as antioxidants, e.g., sodium metabisulfite or ascorbic acid, may also be included in the ophthalmic solutions and ophthalmic ointments. The vehicle for an aqueous solution is of course water. For ointments, vehicles can be white petrolatum, anhydrous liquid lanolin, mineral oil, a nonionic lanolin derivative, or another emulsifying agent. It should be understood that various changes can be made in the selection of the above inactives and excipients (e.g., equivalents may be substituted, changes made in materials, etc.) to adapt to a particular formulation objective.

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (1):

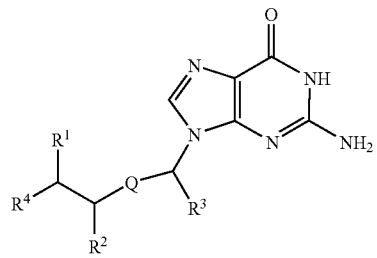

(I)

wherein $R^1$ is H, $(C_1-C_4)$alkyl, $(C_3-C_6)$cycloalkyl, hydroxy$(C_1-C_4)$alkyl, benzoyl$(C_1-C_4)$alkyl or phenyl; $R^2$ is H, OH, hydroxy$(C_1-C_4)$alkyl, $(C_1-C_4)$alkyl or —$CH_2R^a$; $R^3$ is H, $(C_1-C_4)$alkyl or hydroxy$(C_1-C_4)$alkyl; $R^4$ is OH or $R^a$; wherein each $R^a$ is independently -Q-X—Y-$Z_{(n)}$-R; each Q is independently S or O; each X, Y and Z is independently Met, Val, Thr, Tyr, Trp, Ser, Ala or Gly; each R is independently H or an amino-protecting group; and each n is independently 0 or 1; wherein at least one of $R^2$ is —$CH_2R^a$ or $R^4$ is $R^a$; or a pharmaceutically acceptable salt thereof.

2. The compound of claim 1 wherein each Q is O.

3. The compound of claims 1 wherein at least one of R, $R^1$, $R^2$, and $R^3$ is H.

4. The compound of claim 3 wherein each Y and X is individually Gly or Val.

5. The compound of claim 4 wherein each R is H, acetyl, or t-butoxycarbonyl.

6. The compound of claim 5 wherein each R is H.

7. The compound of claim 1 wherein each n is 0.

8. The compound of claim 1, of formula (IV):

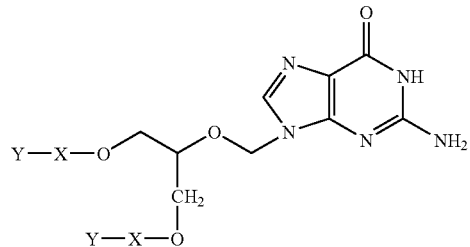

wherein Y—X— is Val-Val-, Val-Gly-, Gly-Val- or Gly-Gly-.

9. The compound of claim 8 wherein Y—X— is Val-Val- or Gly-Gly-.

10. The compound of claim 1 wherein $R^2$ is $CH_2OH$ and $R^4$ is $R^a$.

11. The compound of claim 1 wherein $R^2$ is $CH_2R^a$ and $R^4$ is $R^a$.

12. The compound of claim 1 wherein $R^2$ is $CH_2R^a$ and $R^4$ is OH.

13. The compound of claim 1 wherein each Y—X— is independently Val-Val-, Gly-Gly-, Val-Gly-, or Gly-Val-.

14. A therapeutic composition comprising an effective anti-viral amount of a compound of claim 1 in combination with a pharmaceutically acceptable carrier.

15. The composition of claim 14 wherein the carrier is a liquid.

16. The composition of claim 14 wherein the carrier is an ointment.

17. A method of treating herpes simplex virus comprising administering to a mammal in need of such treatment an effective amount of a compound of claim 1.

18. The method of claim 17 wherein the mammal is a human.

19. The method of claim 17 wherein the herpes virus is HSV-1.

20. The method of claim 17 wherein the herpes virus is HSV-2.

21. The method of claim 17 wherein the herpes virus is human cytomegalovirus and the compound is a compound of claim 1.

22. The method of claim 17 wherein the compound is administered to the eye in eyedrops.

23. The method of claim 17 wherein the effective amount is up to about 20 mg/ml of the compound.

24. The method of claim 17 wherein the infection is an infection of the eye.

25. The method of claim 24 wherein the infection is an infection of the retina.

26. The method of claim 17 wherein the compound is administered systemically.

27. The method of claim 17 wherein the compound is administered orally.

* * * * *